United States Patent
Popa et al.

(10) Patent No.: US 12,279,790 B2
(45) Date of Patent: Apr. 22, 2025

(54) APPARATUS FOR ORIENTATION DISPLAY AND ALIGNMENT IN PERCUTANEOUS DEVICES

(71) Applicant: Stent Tek Limited, London (GB)

(72) Inventors: Sorin Popa, London (GB); Robert Dickinson, London (GB)

(73) Assignee: Stent Tek Limited, London (GB)

( * ) Notice: Subject to any disclaimer, the term of this patent is extended or adjusted under 35 U.S.C. 154(b) by 681 days.

(21) Appl. No.: 17/049,324

(22) PCT Filed: Apr. 23, 2019

(86) PCT No.: PCT/GB2019/051132
§ 371 (c)(1),
(2) Date: Oct. 20, 2020

(87) PCT Pub. No.: WO2019/202339
PCT Pub. Date: Oct. 24, 2019

(65) Prior Publication Data
US 2021/0244434 A1  Aug. 12, 2021

(30) Foreign Application Priority Data

Apr. 20, 2018  (GB) .................................... 1806457
Apr. 24, 2018  (GB) .................................... 1806642
Apr. 24, 2018  (GB) .................................... 1806644

(51) Int. Cl.
*A61B 5/00* (2006.01)
*A61B 17/00* (2006.01)
(Continued)

(52) U.S. Cl.
CPC .... *A61B 17/3403* (2013.01); *A61B 17/00234* (2013.01); *A61B 17/11* (2013.01);
(Continued)

(58) Field of Classification Search
CPC ..................................................... A61B 34/20
See application file for complete search history.

(56) References Cited

U.S. PATENT DOCUMENTS 5,830,222 A   11/1998  Makower
6,475,226 B1  11/2002  Belef et al.
(Continued)

FOREIGN PATENT DOCUMENTS

CN   102272556 A   12/2011
CN   102294896 A   12/2011
(Continued)

OTHER PUBLICATIONS

International Search Report and Written Opinion mailed Aug. 19, 2019 in corresponding International Application No. PCT/GB2019/051132 (19 pages).
(Continued)

*Primary Examiner* — Rajeev P Siripurapu
(74) *Attorney, Agent, or Firm* — Michele V. Frank; Venable LLP

(57) ABSTRACT

Aspects of the present invention relate to an apparatus for determining alignment between a source device and a target device. The apparatus comprises the source device, the target device, and a processing system. The source device comprises a first spatially variant field generator for generating a first spatially variant electric field, and a second spatially variant field generator for generating a second spatially variant electric field, wherein the second spatially variant electric field is angularly offset with respect to the first spatially variant electric field. The target device comprises at least one sensor configured to detect a first signal from the first spatially variant electric field and a second signal from the second spatially variant electric field. The processing system is configured to determine alignment between the first source device and the target device based
(Continued)

on the first and second signals from the first and second spatially variant electric fields by the target device. The inventions further relate to the method of use of the apparatus and the processing system of the apparatus.

35 Claims, 19 Drawing Sheets

(51) Int. Cl.
    *A61B 17/11*     (2006.01)
    *A61B 17/34*     (2006.01)
    *A61B 34/20*     (2016.01)
    *A61B 90/00*     (2016.01)

(52) U.S. Cl.
    CPC .......... *A61B 17/3478* (2013.01); *A61B 34/20* (2016.02); *A61B 90/06* (2016.02); *A61B 2017/00252* (2013.01); *A61B 2017/1107* (2013.01); *A61B 2017/1139* (2013.01); *A61B 2034/2053* (2016.02); *A61B 2034/2072* (2016.02); *A61B 2090/067* (2016.02)

(56) References Cited

U.S. PATENT DOCUMENTS

| | | | |
|---|---|---|---|
| 8,523,800 | B2 | 9/2013 | Brenneman et al. |
| 10,517,637 | B2 * | 12/2019 | Dickinson .......... A61B 17/3415 |
| 10,881,429 | B2 | 1/2021 | Dickinson et al. |
| 2004/0078046 | A1 | 4/2004 | Barzell et al. |
| 2008/0171944 | A1 | 7/2008 | Brenneman et al. |
| 2008/0194939 | A1 | 8/2008 | Dickinson et al. |
| 2009/0096443 | A1 | 4/2009 | Anderson |
| 2010/0158331 | A1 * | 6/2010 | Jacobs ................. H01Q 1/2208 382/128 |
| 2010/0209318 | A1 | 8/2010 | Grande et al. |
| 2010/0230588 | A1 | 9/2010 | Atkinson et al. |
| 2011/0060264 | A1 | 3/2011 | Porter et al. |
| 2011/0316940 | A1 | 12/2011 | Nakakubo |
| 2012/0302935 | A1 | 11/2012 | Miller et al. |
| 2013/0281998 | A1 | 10/2013 | Kellerman et al. |
| 2013/0317334 | A1 | 11/2013 | Bar-Tal et al. |
| 2014/0221803 | A1 | 8/2014 | Bar-Tal |
| 2015/0223729 | A1 | 8/2015 | Balachandran et al. |
| 2015/0374486 | A1 | 12/2015 | Dickinson et al. |
| 2016/0045133 | A1 | 2/2016 | Balachandran |
| 2018/0000512 | A1 | 1/2018 | Dickinson |

FOREIGN PATENT DOCUMENTS

| | | |
|---|---|---|
| CN | 102939051 A | 2/2013 |
| EP | 1891895 A1 | 2/2008 |
| EP | 2528503 B1 | 7/2014 |
| JP | 4025309 B2 | 12/2007 |
| JP | 2008511414 A | 4/2008 |
| JP | 2013248388 A | 12/2013 |
| WO | 1997/013471 A1 | 4/1997 |
| WO | 9713463 | 4/1997 |
| WO | 2000/045886 A2 | 8/2000 |
| WO | 2002/062265 A2 | 8/2002 |
| WO | 2006026687 A2 | 3/2006 |
| WO | 2006027599 A1 | 3/2006 |
| WO | 2008092246 A1 | 8/2008 |
| WO | 2008097767 A2 | 8/2008 |
| WO | 2010052480 A2 | 5/2010 |
| WO | 2011092613 A1 | 8/2011 |
| WO | 2011159621 A2 | 12/2011 |
| WO | 2014005155 A1 | 1/2014 |
| WO | 2014137830 A1 | 9/2014 |
| WO | 2016145202 A1 | 9/2016 |

OTHER PUBLICATIONS

Combined Search and Examination Report mailed Apr. 26, 2016 in UK Application No. GB1604107.1 (7 pages).
International Search Report and Written Opinion in corresponding International Application No. PCT/US2016/021782 mailed Jun. 30, 2016 (10 pages).
European Search Report mailed Nov. 15, 2018 for European Application No. 16762517.7 (12 pages).
Examination Report under sections 12 & 13 mailed Jul. 8, 2022, directed to IN Application No. 202027048884; 8 pages.

* cited by examiner

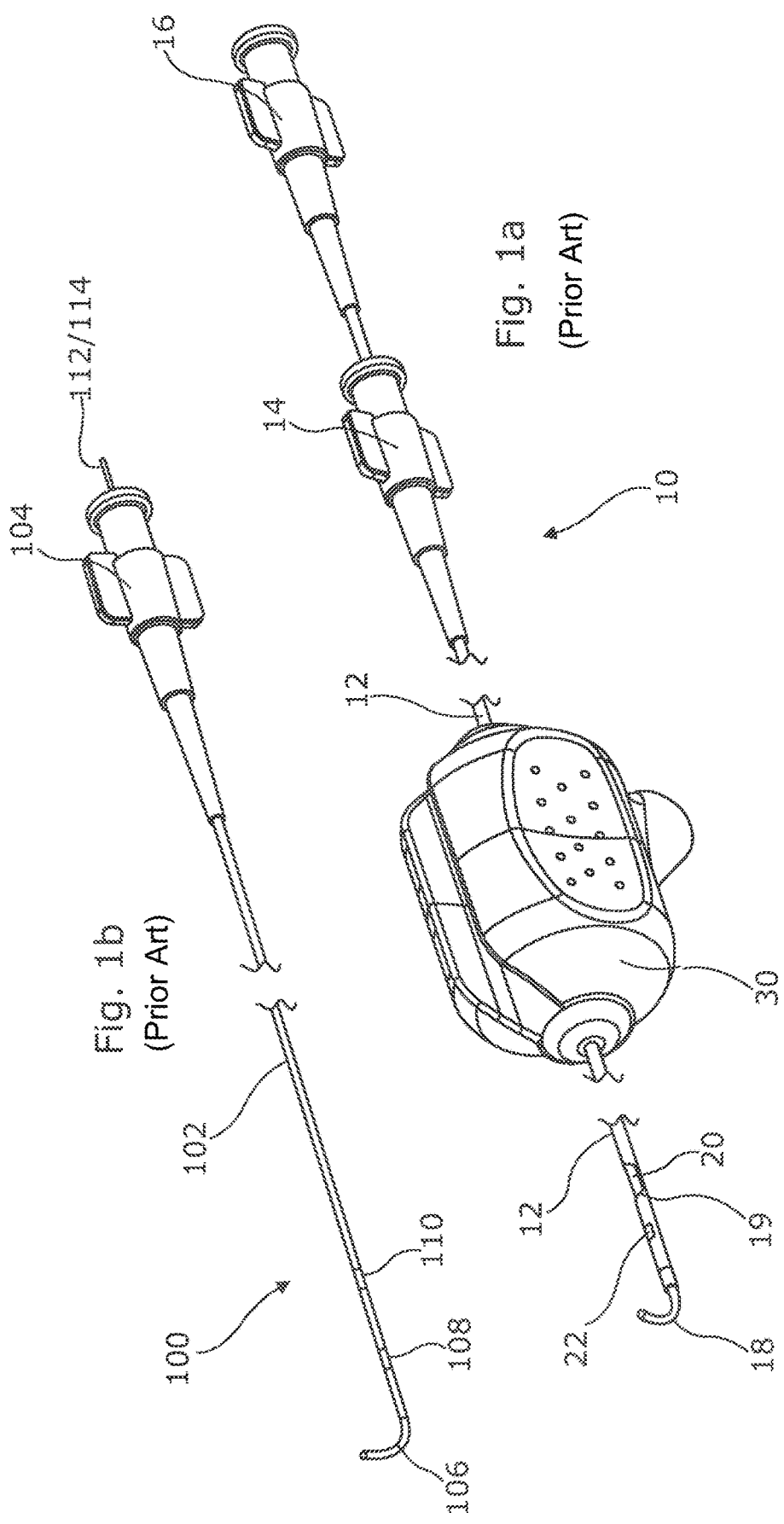

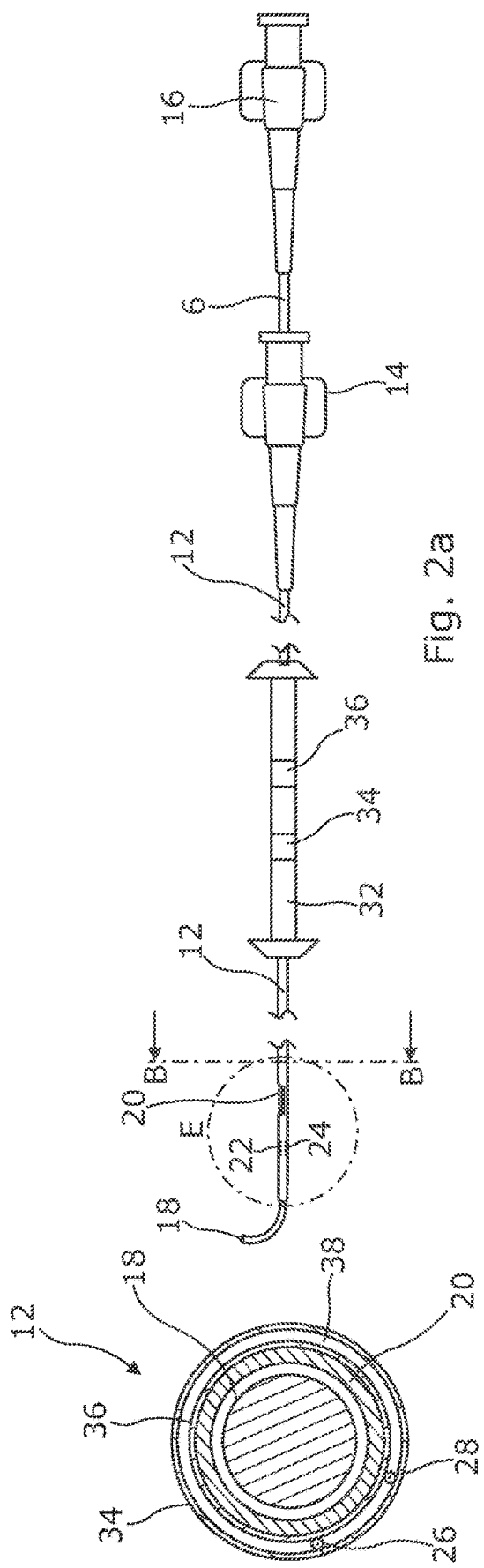
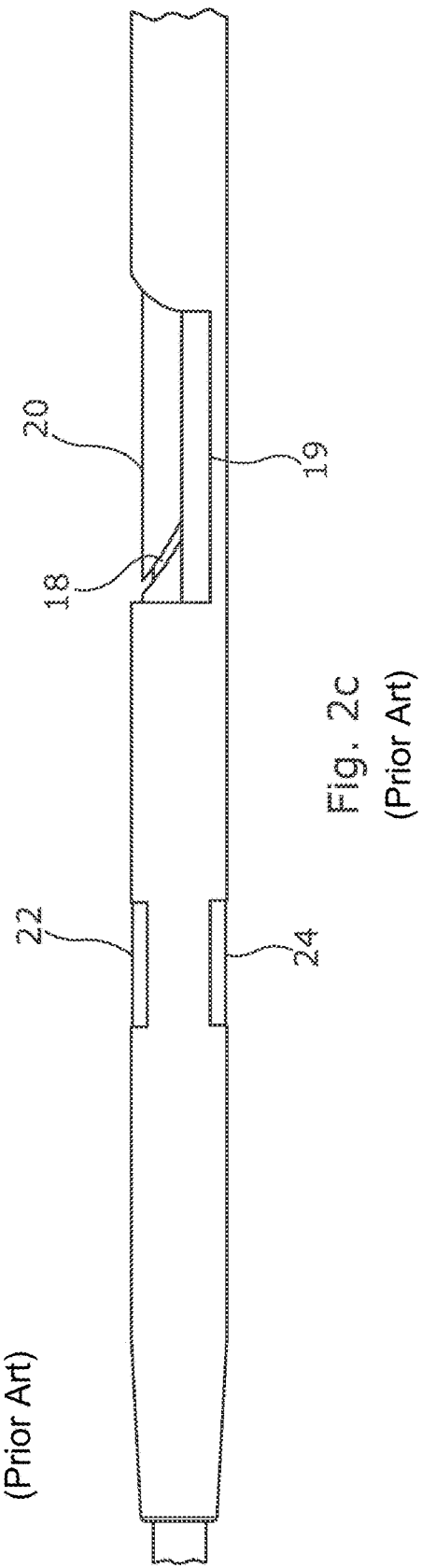
Fig. 2a (Prior Art)
Fig. 2b (Prior Art)
Fig. 2c (Prior Art)

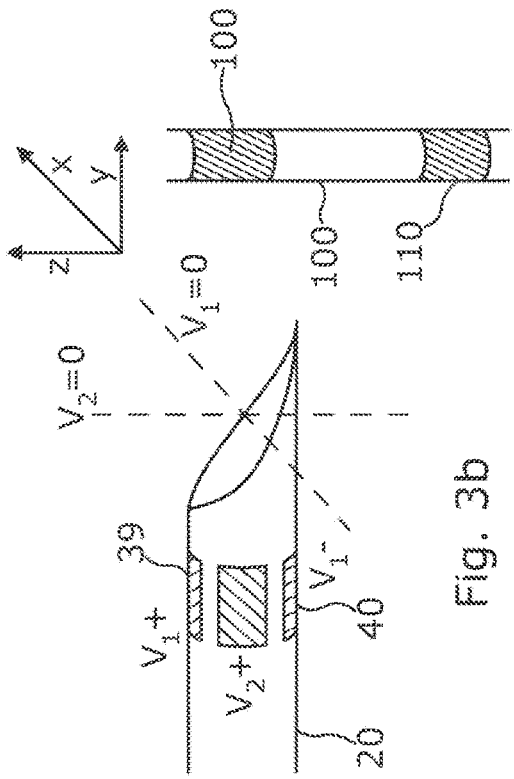
Fig. 3a (Prior Art)
Fig. 3b (Prior Art)
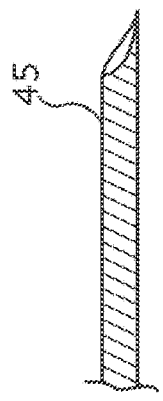
Fig. 3e (Prior Art)
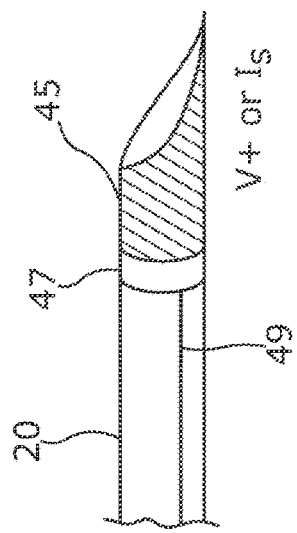
Fig. 3d (Prior Art)
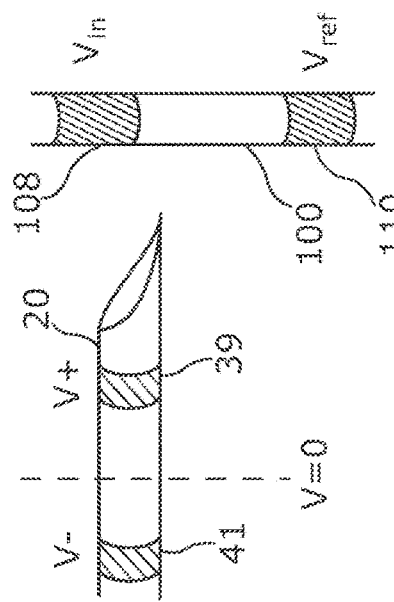
Fig. 3c (Prior Art)

APPARATUS FOR ORIENTATION DISPLAY AND ALIGNMENT IN PERCUTANEOUS DEVICES

CROSS-REFERENCE TO RELATED APPLICATIONS

This application is a National Stage Application under 35 U.S.C. § 371 to PCT/GB2019/051132, filed Apr. 23, 2019, which claims priority from Great Britain Application No. 1806457.6, filed Apr. 20, 2018, Great Britain Application No. 1806644.9, filed Apr. 24, 2018, and Great Britain Application No. 1806642.3, filed Apr. 24, 2018, the entire content of which is incorporated herein by reference. All references cited anywhere in this specification, including the Background and Detailed Description sections, are incorporated by reference as if each had been individually incorporated.

FIELD

The invention relates to the apparatus and methods used in the minimally invasive creation of conduits, openings or fistula between adjacent body cavities (anastomoses). In particular, the invention relates to the apparatus and methods used in the minimally invasive creation of anastomoses, and more particularly to the creation of anastomoses using catheters and alignment methodology.

BACKGROUND

Minimally invasive surgery is a common method to perform a variety of cardiovascular and endoscopic procedures. It is typically performed using catheters that are inserted into various lumens or other cavities within the body through small incisions in the skin. A percutaneous approach to the creation of conduits, openings, or fistula (anastomoses) has several clinical benefits including simplifying the procedure and reducing surgical trauma to the cavities or vessels which has a negative effect on patency.

Several technologies have been developed with the purpose of creating anastomoses percutaneously however none have been approved for clinical use. All of the following technologies employ one or two catheters in order to create an anastomosis between two adjoining blood vessels. U.S. Pat. No. 8,523,800 describes technology for forming a fistula with the aim of treating COPD patients and those with hypertension. U.S. Pat. No. 5,830,222 describes technology for percutaneously connecting two vessels to divert arterial blood to the venous system, and U.S. Pat. No. 6,475,226 describes an alternative to coronary bypass surgery. US2013/0281998 and US2012/0302935 describe technologies for percutaneously creating fistulas for dialysis use.

One approach to using intravascular or endoscopic catheters for creating an anastomosis involves placing a tube or stent graft between the two body cavities (i.e. two lumens) in order to form the connection. This requires an active means to align the two catheters, as fluoroscopy is not adequate for the angular alignment.

In minimally invasive and percutaneous interventions as described above, there is a need to align one interventional device relative to another.

It is known that directional alignment can be achieved using a beam-like energy source, i.e. laser which function like a rotating lighthouse beacon (i.e. no or minimal signal for most of the source device rotation and then a bright peak once it points in the right direction). The measured signal in this approach would resemble a gaussian approximation of an impulse-function.

Alternatively, alignment of a source device to a target device can be achieved by transmitting a directional or asymmetric signal or field from a source device and receiving a signal in the neighbouring target device. Rotating or otherwise moving the source device so that the received signal will indicate alignment. This technique has been described with reference to a number of different technologies including electric fields (WO2016/145202). The alignment can be used to guide the advancement of a penetrating device such as a needle from one device to another, for example, as a precursor to inserting a stent graft to make a channel from one cavity to another (WO 97/13463).

The process of rotating until a maximum signal is obtained has a number of disadvantages. In some cases the maximum may be shallow so that the alignment may not be sensitive to changes in angle leading to inaccurate alignment. In finding the maximum it is necessary to rotate the source device until the maximum is reached and then passed, so the signal starts decreasing from the maximum, this means the process of locating the maximum requires a number of iterative movements in both directions until the operator homes in on the maximum signal. In addition when the first signal is obtained it is not apparent which direction to turn the source device and this may result in significant rotation to find a signal before attempting to maximise it.

Moreover, the purpose of rotationally aligning a source device relative to a target device is to accurately direct a penetrating member (i.e. crossing member), such as a needle, from the source catheter in a lumen of a cavity or vessel to a lumen of a cavity or vessel in which the target catheter is located. If the target catheter is not properly centred within the lumen in which it resides there is an increased risk of the crossing member missing the lumen completely even if the crossing member was initially aligned to the target catheter. In addition, a means of sensing and/or capturing the penetrating member once it has reached the target body cavity would be desirable.

Additionally, the generation of the asymmetric electric field that is aligned with the needle placement requires accurate positioning of electrodes on the source device. Current production methods are limited for catheters with a small diameter, and typically require manual assembly/ placement of conductive foil which is limited in reproducibility and accuracy.

It is an object of the invention to address at least some of the disadvantages associated with the prior art.

SUMMARY OF THE INVENTION

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

According to a first aspect of the invention, there is provided apparatus for determining alignment between a source device and a target device. The apparatus comprises the source device, the target device, and a processing system. The source device comprises a first spatially variant field generator for generating a first spatially variant electric field, and a second spatially variant field generator for generating a second spatially variant electric field, wherein the second spatially variant electric field is angularly offset with respect to the first spatially variant electric field. The target device comprises at least one sensor configured to detect a first signal from the first spatially variant electric field and a second signal from the second spatially variant electric field. The processing system is configured to determine alignment between the first source device and the target device based on the first and second signals from the first and second spatially variant electric fields detected by the target device.

In an embodiment, each of the first spatially variant field and the second spatially variant field may have a known angular dependence. In another embodiment, the first spatially variant electric field may be angularly offset from the second spatially variant electric field by a preset or known angle. Suitably, the preset angle may be 90°.

In a further embodiment, the first spatially variant field generator and the second spatially variant field generator may each be at least one electrode. Suitably, the first spatially variant field generator and the second spatially variant field generator may each be at least two electrodes.

Suitably, the at least one electrode of the first spatially variant field generator is arranged to produce the first spatially variant electric field with angular and/or spatial dependence; and wherein the at least one electrode of the second spatially variant field generator is arranged to produce the second spatially variant electric field with angular and/or spatial dependence.

In an embodiment, the first spatially variant electric field and the second spatially variant electric field with angular and/or spatial dependence are fields independently selected from the group comprising: dipole; quadrupole; and octopole.

Suitably, the at least one electrode of the first spatially variant field generator and the at least one electrode second spatially variant field generator may be each separately arranged to produce a dipole field.

In an embodiment, the processing system may be capable of operating the source device in at least a first mode and a second mode, wherein in the first mode, the first spatially variant field generator generates the first spatially variant electric field, and wherein in the second mode, the second spatially variant field generator generates the second spatially variant field.

In an embodiment, the processing system may further comprise a first switching system connected to the first spatially variant field generator and the second spatially variant field generator on the source device, the first switching system configured to operate the source device between the first mode and the second mode.

In an embodiment, the switching system may operate the source device sequentially in the first mode and the second mode.

In an embodiment, the source device may be operated in the first mode until coarse alignment is achieved, and then the source device is operated in the second mode to achieve fine alignment, wherein coarse alignment has a lower degree of accuracy in the angle of alignment of the source device in comparison to fine alignment.

In an embodiment, the first switching system may toggle between the first mode and second mode so that a signal can be detected from both the first spatially variant field and the second spatially variant field simultaneously.

In an alternative embodiment, the first switching system may operate the source device concurrently in the first mode and the second mode. In this embodiment, suitably, the first spatially variant electric field and the second spatially variant electric field may be distinguishable by the sensor on the target device. More suitably, the first spatially variant electric field and the second spatially variant electric field may be distinguishable by the sensor on the target device due to the first spatially variant electric field and the second spatially variant electric field having a different carrier frequency.

In embodiments, the sensor on the target device may be connected to a processing system via a second switching system, wherein the second switching system diverts the detected spatially variant signal detected or sensed at the sensor to one of two memory locations, wherein the second switching system is controlled to divert the detected signal to a first memory location of the two memory locations when the first switching system is operating in the first mode, and the second switching system diverts the detected signal to a second memory location of the two memory locations when the first switching system is operating in the second mode.

Suitably, the second switching system may be of a type selected from the group consisting of: hardware and software.

According to another aspect of the invention, there is provided a method for determining an angle of alignment between a source device and a target device, the source device comprising a first spatially variant field generator for generating a first spatially variant electric field, and a second spatially variant field generator for generating a second spatially variant electric field, wherein the second spatially variant electric field is angularly offset with respect to the first spatially variant electric field, the target device comprising at least one sensor configured to detect a first signal from the first spatially variant electric field and a second signal from the second spatially variant electric field. The method comprises:

a) generating a first spatially variant electric field from the first spatially variant field generator on the source device;
b) detecting the signal of the first spatially variant electric field using the sensor on the target device to provide a first spatially variant signal;
c) generating a second spatially variant electric field from the second spatially variant field generator on the source device;
d) detecting the signal of the second spatially variant electric field using the sensor on the target device to provide a second spatially variant signal;
subsequently followed by:
e) determining the alignment angle between the source device and the target device as a function of the detected signals for the first spatially variant electric field and the second spatially variant electric field.

In embodiments, step (a) precedes step (b); step (c) precedes step (d). Steps (a) and (b) and steps (c) and (d) may be performed sequentially (i.e. step (a) if followed by step (b), which is followed by step (c) which is followed by step (d)); reverse sequentially (i.e. step (c) is followed by step (d), which is followed by step (a) which is followed by step (b); or simultaneously (i.e. steps (a) to (d) are all performed at the same time). Suitably, all of steps (a) to (d), whether performed once or repeated, precede step (e).

Suitably, steps (a) to (d) are performed concurrently. Alternatively, when steps (a) to (e) are performed sequentially, after step (b) the first spatially variant electric field is switched off prior to the signal being generated by the second spatially variant electric field.

In another embodiment, steps (a) to (d) may be repeated.

In an embodiment, the alignment angle may be calculated as a function of the detected signals in steps (b) and (d) using the formula:

alignment angle=function(first spatially variant signal, second spatially variant signal)

In another embodiment, when the first spatially variant electric field is angularly offset from the second spatially variant electric field by approximately 90° the alignment angle is calculated as a function of the detected signals in steps (b) and (d) using the formula:

alignment angle=arctan(first spatially variant signal, second spatially variant signal 2).

In a further embodiment, the angular dependence of the first spatially variant field and the second spatially variant field is the same and/or the angular dependence of the first spatially variant field and the second spatially variant field is sinsusoidal.

In an embodiment, the desired alignment angle is offset from that indicated by the first spatially variant electric field and the second spatially variant electric field by an angle defined by an offset angle, the alignment angle is calculated as a function of the detected signals in steps (b) and (d) using the formula:

alignment angle=offset angle+arctan(first spatially variant signal, second spatially variant signal).

In an embodiment, the alignment angle is displayed on a display.

According to third aspect of the invention, there is provided a processing system for use in the apparatus described above and/or configured to perform the method described above.

In an embodiment of the first aspect of the invention or the third aspect of the invention, the apparatus or the processing system may further comprising a display.

Also described herein is a target device comprising a self-centring mechanism (SCM) for positioning the alignment centre of the target device towards or at the centre of a target lumen in which it is located. Suitably, the SCM may comprise radially expandable members. Suitably, the SCM may comprise 2, 3, 4, 5, 6, 7, 8, 9, 10, 15, 20, 25, 30, 35, 40, 45, 50 or more radially expandable members. Suitably, the radially expandable members are of substantially equal stiffness. In examples, the radially expandable members are arranged in a substantially rotationally symmetrical orientation around a central longitudinal axis. Suitably each of the radially expandable members of the SCM, when deployed, are arcuate extending from a fixed proximal point at one end to a fixed distal point at the other.

In examples, the SCM is located at a distal end of an elongate shaft of the target device, suitably a catheter. The target device may have a lumen that extends along the length of the elongate shaft. In examples, the SCM has a first retracted position or configuration and a second deployed position or configuration, wherein, in examples, the SCM is radially expandable from the first retracted position to the second deployed position to position the end of the elongate shaft of the catheter in centre of the vessel or lumen or cavity in which it is located. The first retracted position may comprise the SCM being entirely or substantially retracted within the lumen on the target device. To achieve the expanded configuration the SCM may be advanced distally out of the lumen of the target device allowing one or more of the radially expandable members to expand radially, suitably from the longitudinal axis of the elongate shaft. Suitably the expansion is to the extent that at least one, suitably at least two, suitably at least three, suitably more than three, suitably each of the radially expandable members, contacts the inner wall of a vessel or cavity in which the target device is located. Suitably, the radially expandable members are formed of shape memory metal, such as Nitinol™ such that movement between the retracted configuration and the expanded configuration is automatic on deployment of the SCM from the target device. The first retracted position may allow passage of the SCM to a target region within the body through relatively narrow vessels, the SCM to be then be deployed into the second deployed position once it has reached the target region.

In examples, the self-centring mechanism may comprise conductive members or alternatively, the radially expandable members, or part thereof, are conductive. Suitably, the conductive members or the conductive radially expandable, members, or part thereof, are arranged circumferentially around a central point or axis to mimic or provide a single sensing electrode at a central point or axis, suitably, the central point or axis of the SCM is substantially, or approximately, equidistant from each of the expandable members.

In examples, the conductive members or the conductive radially expandable members, or part thereof, are configured to act as a sensor to detect contact with a device, such as a penetrating member, that has entered the vessel or cavity in which the target device is located. Suitably, the SCM conductive members or the conductive radially expandable members are also, or alternatively, configured to detect the device penetrating member as it leaves the lumen in which the target device is located.

In examples the SCM is configured to capture or snare a guide wire or other suitable object present in or conveyed to the target device. The capture may suitably be by retraction of the SCM into the lumen of the target device once the guide wire or other suitable object has passed between at least two radially expandable members.

This description also relates to a method of use of the target device comprising an SCM to detect the presence and/or position of a penetrating member, and to capture a guide wire. This description also relates to a method of manufacture of the SCM and the target device comprising the SCM.

Also described herein is a method for the creation of electrodes on a small diameter curved surface, such as that of a catheter. Suitably, the method provides sufficient accuracy in the creation of the electrodes on a catheter that they may guide the creation of a conduit between two vessels or cavities (an anastomosis). Suitably, the accuracy of placement should be better than 10 micron resolution and rotationally aligned to within 1 degree relative to their nominal positions on the cardinal points.

In another example the printing method can comprise a continuous fluid extrusion. The printing method may be similar to that described in application US20100209318A1, the details of the methods of printing described therein are incorporated herein by reference.

In an example the elements and tracks are made with a silver based ink, as a base, with a gold based ink printed on top. Suitably, an insulating material, such as polyurethane, can be printed selectively on top of the conductive tracks to expose only certain elements.

In another example a primer is printed on the catheter tube, and subsequent immersion in an electro-less plating solution can deposit an electrode pattern.

In another example a primer is printed on the catheter tube then activated with a laser, and subsequent immersion in an electro-less plating solution can deposit an electrode pattern.

In another example, a mask containing a negative of the electrode pattern can be used, through which a metal such as gold, or silver, can be applied to the polymer substrate using sputter deposition (a form of physical vapour deposition (PVD)).

In another example, a metal such as gold or silver, can be applied to the polymer substrate using sputter deposition after which a laser beam can be used to selectively ablate the metalized coating creating the electrode pattern.

The method may comprise rotating the catheter and printing the electrode onto the surface of the catheter during rotation. The printing process may comprise an inkjet printing process of suitable conductive material.

Suitably the ink comprises silver particles or gold particles or other conductive materials. The ink can also comprise a polymer medium which when cured remains flexible.

BRIEF DESCRIPTION OF THE DRAWINGS

One or more embodiments of the invention will now be described, by way of example only, with reference to the accompanying drawings, in which:

FIG. 1 is a representation of an embodiment of an apparatus comprising a source catheter (FIG. 1a), a sensing/target catheter (FIG. 1b), and a handle and a user interface of the device.

FIG. 2a is a more detailed representation of the source catheter of FIG. 1.

FIG. 2b is a cross sectional representation of the source catheter of FIG. 2a along the line of BB.

FIG. 2c is an expanded view of the distal end of the source catheter within the circle E in FIG. 2a.

FIG. 3a is a representation of an embodiment of the apparatus with signal source electrodes arranged on the penetration member, and the sensing catheter.

FIG. 3b is a representation of an embodiment of the apparatus with two pairs of signal source electrodes arranged on the penetration member in a diametrically opposed fashion, and the sensing catheter.

FIG. 3c shows a cross-sectional view of the penetrating member shown in FIG. 3b.

FIG. 3d is a representation of an embodiment of the apparatus with a single source electrode forming the tip of the penetrating member.

FIG. 3e is a representation of an embodiment of the apparatus with a single source electrode comprising of the entire length of the penetrating member.

FIG. 7a or 7b is switched to the first mode.

DETAILED DESCRIPTION

Figure 2D:
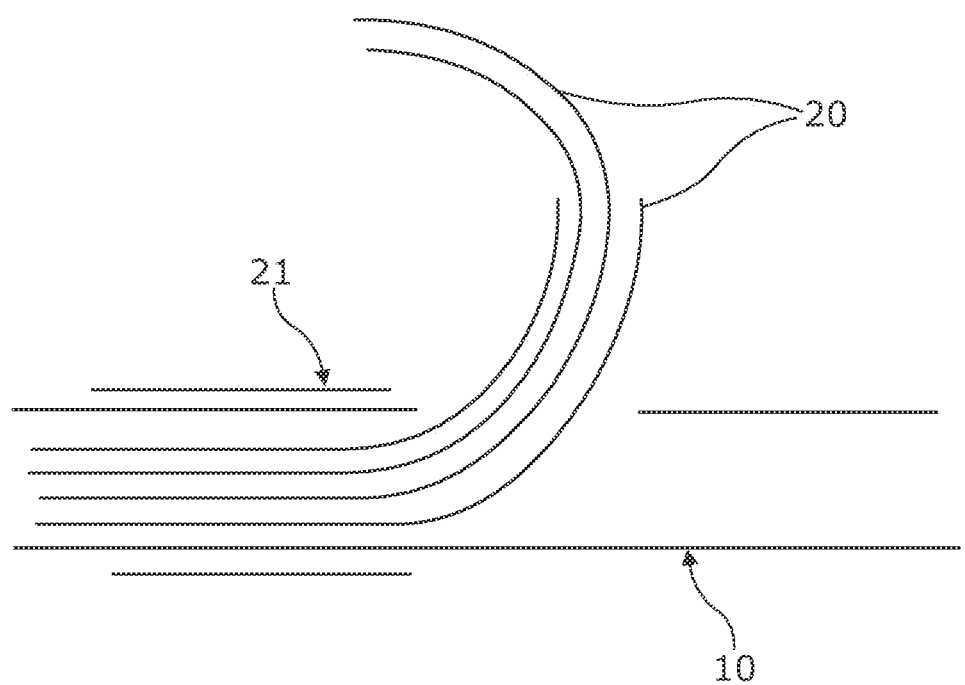

All references cited herein are incorporated by reference in their entirety. Unless otherwise defined, all technical and scientific terms used herein have the same meaning as commonly understood by one of ordinary skill in the art to which this invention belongs.

The invention provides for improvements in apparatus in the form of medical devices, typically in the context of a catheter that comprises functional elements at the distal portion and a user or operator interface at the proximal terminus. The improvements of the invention generally relate to the fine control of alignment and an improved method of identifying optimal alignment; apparatus to improve the centering of the target device in a target lumen, a means of sensing successful penetration of the target lumen and capturing or snaring the penetrating member or materials passed to the target lumen after successful crossing; and an improved process for the accurate application of electrodes and/or additional conductive supporting circuitry to a curved catheter surface.

Prior to setting forth the invention, a number of definitions are provided that will assist in the understanding of the invention.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

As used herein the terms distal and proximal are used to refer to orientation along the longitudinal axis of the apparatus. Since the devices of the invention are elongate in nature and conform to a single dimension, in use the distal direction refers to the end of the device furthest away from the operator and the proximal direction the end of the device closest to the operator. It should be noted that the term proximal should not be confused with the term 'proximate', which adopts its conventional meaning of 'near to'.

As used herein, the term "catheter" refers to a device that comprises an elongated shaft. The shaft is typically is provided with a central lumen that extends along its entire length. The elongate shaft of embodiments of the invention are suitably constructed as catheters in a variety of sizes typically ranging from about 0.15 mm up to about 12 mm or more in diameter (corresponds to French sizes 0.5 to 34). Suitably, the upper limit of the diameter of the catheter may be about 4 mm, 5 mm, 6 mm, 7 mm, 8 mm, 9 mm, 10 mm, 11 mm or more (corresponds to French sizes 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 20, 31. 32, 33, 34 or more) The elongate shaft is suitably constructed from a polymeric material such as a silicone rubber or a polymer including thermoplastic elastomer, PEEK, polyimide, high density polyethylene (HDPE), Pebax, and/or nylon; or composites thereof. All or a portion of the shaft may also comprise a low friction or lubricious coating that may, for example, include a fluoropolymer such as a PTFE or parylene. All or a portion of the shaft may also be reinforced using various arrangement of metallic filaments. All or a portion of the shaft may also be replaced by laser cut metallic tubing such as nickel titanium alloy, stainless steel, or other biocompatible metal alloys.

As used herein "centre" or "centred" or "centring" refers to positioning away from the sides of the lumen of a cavity or vessel. It can mean positioning exactly in the centre of the lumen (i.e. equidistant from each side of the lumen) or substantially in the centre of the lumen (i.e. close to the exact centre of the lumen, suitably within 5%, 10%, 15%, 20%, 25%, 30%, 35%, 40%, 45% or 50% of the radius of the lumen from the exact centre, more suitably within 25% of the radius of the lumen from the exact centre, even more suitably within 10% of the radius of the lumen from the exact centre). In irregularly shaped lumens, the term may refer to the centroid or the geometrical centre of the lumen, or part thereof.

As used herein, the terms "asymmetric signal", "asymmetric field", "directional signal", "directional field", "spatially variant signal", "spatially variant field", "spatially variant field" or "field with spatial variance" are intended to be used interchangeably and mean signals or fields having at least one property that, when measured has spatial variance (i.e. is asymmetric, or has one or more asymmetries, with respect to the measurable signal in at least one given plane or on at least one axis of rotation of the field). The spatial variance or asymmetry may, for example, be in the amplitude and/or polarity of the voltage of the field. For example, a dipole field formed between two electrodes on a catheter is an asymmetric field by virtue of the asymmetry in the polarity of its measurable voltage on either side of the plane formed equidistant from each electrode. Suitably, the amplitude of the electric field may vary sinusoidally when its position is varied relative to a sensor (i.e. the field may have 'sinuosidal dependence' with the angle relative to one of the electrodes). An asymmetric or spatially variant field may have a property, such as amplitude or polarity of the field, for example, the voltage, at a given point, whose value varies as the field, and/or the electrodes generating the field are angularly or longitudinally displaced relative to that point. In such situations the asymmetric field may be described as having an 'angular dependence' or a 'spatial dependence' for example a 'longitudinal dependence'. In all cases, where a field has a particular dependence, the electric field varies asymmetrically or non-uniformly relative to the electrodes creating it when measured depending on an aspect of its orientation or position. In all cases, asymmetry or spatial variance means that the field or signal is not uniform when the signal generator on a source catheter is, or signal generating electrodes on a source catheter are, moved around a given axis and/or translates in space relative to the receive electrode(s) in the sensing catheter.

An "asymmetric electric field" or a "spatially variant electric field" or a "spatially variant field" is an asymmetric field having the properties of an electric field having an asymmetric or spatially variant signal as defined above. This should be contrasted with an electric field generated between two opposing plates, whose size is large compared to their separation, where movement of a sensor within the field experiences no changes in a chosen parameter.

As used herein, a 'sinusoidal waveform' means a wave form that describes a smooth repetitive oscillation in which the amplitude is always proportional to sine (sin) or cosine (cos) of its displacement angle at a given point of time. The term "sinusoidal waveform" may relate to a single sin or cos wave or a combination of these waves. In its most basic form, a sinusoidal waveform as a function of time (t) is:

$$Y(t) = A \sin(2\pi f t + \varphi) = A \sin(\omega t + \varphi)$$

Where, A is the amplitude, f is the frequency, $\omega = 2\pi f$ is the angular frequency, and q is the phase.

References to zero values, null values, minimum values, maximum values, or any other values are envisaged as values of voltage amplitude or other properties of electric fields unless stated otherwise. References to detection of an asymmetric electric field or similar are also intended to mean detection of a parameter or property of the asymmetric electric field and a measurement of its amplitude.

As used herein, the term "display" or "to display" means a device or action that presents the alignment angle in a suitable analogue or digital manner to a user. The alignment angle may be shown as a numerical or graphical representation. Such display may also include a visual indication of when optimal/poor alignment is achieved such as a colour change, flashing, a sound, graphical representation etc. The display may be in the form of a screen or other suitable visual and/or audible display equipment.

The Surgical Device and Method of Use

The present invention relates to advancements in the apparatus and methods described in WO2016/145202, the disclosure of which is herein incorporated in its entirety.

In an example, the prior art apparatus comprises three main components: a source catheter, a sensing catheter, and an electronic alignment monitor system. In one example the source catheter may be located within a first body cavity (or lumen or vessel) and the sensing catheter may be located within an adjacent second body cavity (or lumen or vessel).

FIG. 1a shows a prior art source catheter 10. The source catheter 10 comprises an elongate body 12 having a proximal and distal end. Toward the proximal end of the body 12 is positioned a first Luer connector 14 in communication with the body 12; and a second Luer connector 16 in communication with the lumen of the penetrating member 20.

The source catheter 10 may further comprise a guide wire 18 that is operable between a retracted position wherein the guide wire 18 is retained within the lumen, and an extended position wherein the guide wire 18 extends outwardly from the distal end of the lumen, and a penetrating member 20. The guide wire 18 runs co-axially within the penetrating member 20 for the entire length of the catheter 10. The penetrating member 20 is constrained inside the catheter 10 to lie along the axis of the catheter 10. The penetrating member 20 has a pre-formed curve at its distal end, so that when it exits the catheter 10 it adopts a shape that curves in a radial direction with respect to the axis of the catheter 10. In the example shown in FIG. 1a, the penetrating member 20 is ejected through an opening or aperture 19 in the side wall of the catheter 10. The aperture 19 may be covered with a sliding cover 21 such as a tube or sleeve (not shown) that can be withdrawn when the penetrating member 20 is ejected. Furthermore, only when the guide wire 18 is in the retracted position can the penetrating member 20 be ejected from the catheter 10.

The penetrating member 20 may be a retractable hollow needle or stylet formed from a suitable material including polyether ether ketone (PEEK), carbon fibre loaded liquid crystalline polymer, tungsten carbide polyimide, stainless steel, gold, platinum, shape memory alloy (including NiTinol™) or other suitable surgically compatible metal alloys. The penetrating member 20 may be provided with a sharp tip at its distal end, which is used to puncture and penetrate tissue at the site of treatment. The lumen of the penetrating member 20 allows the delivery of a standard guide wire 18 from one vessel to another.

As best shown in FIGS. 2a and 2c, toward the distal end of the body 12 there are positioned a pair of electrodes 22, 24 spatially separated around the circumference of the body 12 such that they are substantially diametrically opposed. The pair of electrodes 22, 24 are arranged along an axis that is substantially aligned with the direction of deployment of the penetrating member when it is extended outwardly from the source catheter. As best seen in FIG. 2a, electrode wires 26, 28 (not shown) extend proximally from the electrodes along the lumen until they connect with pads 34 and 36 on the rigid clip-on section 32.

As shown in the example in FIG. 1a, a handle 30 provides a first user interface with the catheter 10. The handle 30 is removably attached to the body 12 via the rigid clip-on section. The handle 30 is arranged on the body 12 so as not to interfere with insertion of the catheter 10 into the body, suitably the handle 30 is positioned toward the proximal end of the body 12. In some examples, the catheter 10 may be arranged to not include the handle 30.

Figures 4A, 4B:
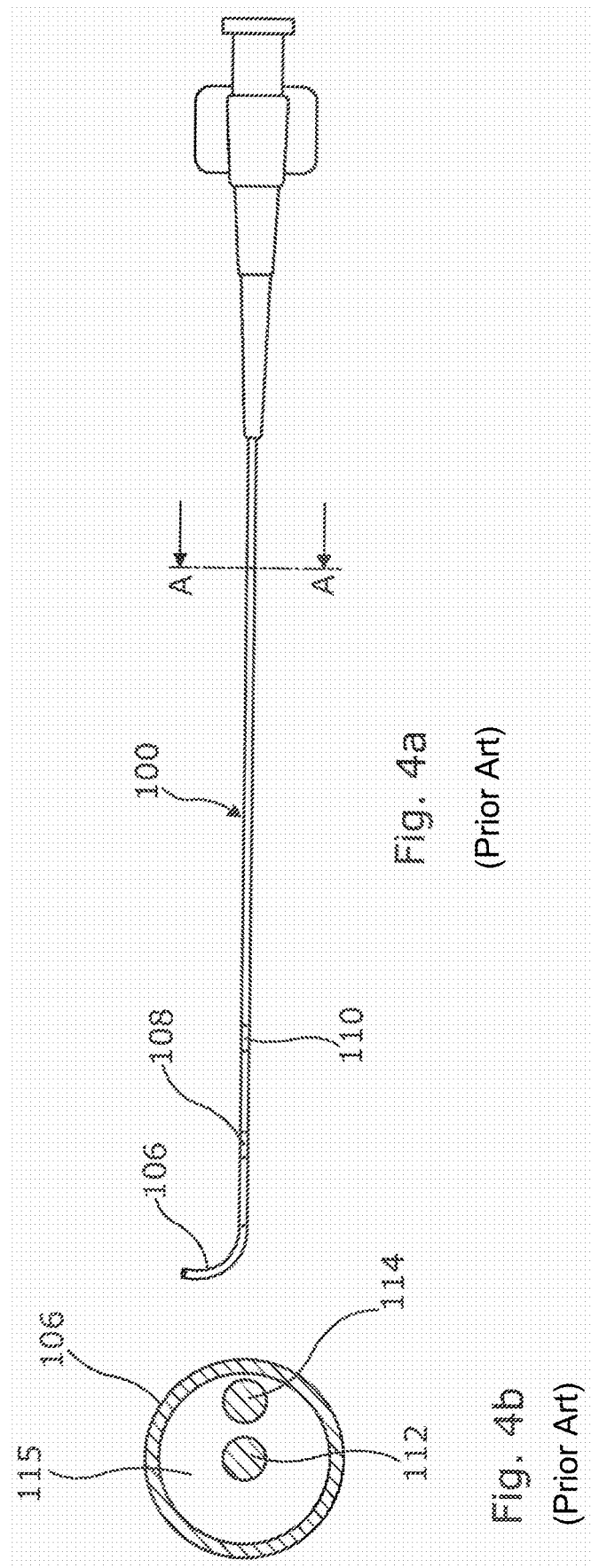
FIG. 4a is a representation of a specific embodiment of the sensing catheter according to an embodiment.
FIG. 4b is a cross sectional representation of the sensing catheter of FIG. 4a along the line of AA.

FIGS. 1b, 4a and 4b show an example of a prior art sensing catheter 100. The sensing catheter 100 comprises an elongate lumen 102 having a proximal and distal end. Toward the proximal end of the lumen 102 is positioned a Luer connector 104.

The sensing catheter 100 comprises a hollow guide wire 106 and two ring electrodes 108, 110. Electrode wires 112, 114, each of which is connected to a respective ring electrode, extend proximally in the interior of the lumen 102 and exit the lumen at the proximal end through the Luer connector 104.

FIG. 2a shows the source catheter 10 in side view with the handle 30 removed. On the body of the catheter 10 there is a rigid clip on section 32 of a larger diameter than the body 12 which comprises two ring electrodes 34, 36. This section is formed so as to mate with the handle 30 and allow for free rotation of the handle through a 360 degree electrical connection.

In one example of the catheter 10 the two electrodes 22, 24 are diametrically opposed each occupying less than half of the circumference of the body 12. In an example, one electrode 22 serves as the positive electrode, and the second 24 serves as a negative electrode, thereby forming a dipole configuration. Several other arrangements are also possible, such as an evenly spaced array of more than two electrodes arranged around the circumference of the body 12, examples of this type would suitably include quadrupole or octopole configurations of electrodes. The electrodes 22, 24 are located distally to the penetrating member 20 along the body of the source catheter 10 in order to be aligned with the end of the penetrating member 20 when ejected. This ensures that point which the penetrating member 20 punctures into the vein corresponds to and is aligned with the position of peak field strength generated by the electrodes. In an alternative example the electrodes 22, 24 can be located proximal to the penetrating member 20.

Electrode wires 26, 28 provide electrical connection from each electrode 22, 24 to a respective ring electrodes 34, 36 in the rigid clip on section 32 positioned towards the proximal end of the catheter 10. In this example the ring electrodes 34, 36 form a convenient rotary connection with the handle 30 when attached to the rigid clip on section 32 thereby preserving electrical connection between the handle 30 and the source catheter 10 through any degree of rotation about the axis of the catheter 10. Other examples using an electrical plug or conventional hub are also suitable.

An expanded view of the distal end of the source catheter 10 is shown in FIG. 2c. The typical spatial arrangement of the two electrodes 22, 24 is shown. In this example, the electrodes 22, 24 are aligned and diametrically opposed on either side of the catheter body 12. In another example the electrode, or each pair of electrodes, are diametrically opposed but not aligned, with one electrode axially offset from the other electrode along the body 12.

In FIGS. 3a to 3e, an example of a prior art penetrating member 20 is shown that may be aligned via one or more asymmetries or spatial variances in an electric field. In this example angular rotation of the source device is not necessarily used for alignment, and instead orientation is based on changes in the measured signal during spatial movement of the penetrating member relative to a sensing catheter 100. The arrangement and positioning of the electrodes on the penetration member 20 are a further example of those that may be applied by the method of the present invention.

As best shown in FIGS. 3a to 3e one or more further electrodes are mounted on the distal end of the penetrating member 20. In this example the entire penetrating member is insulated except for a section of the distal end that forms an electrical connection to the penetrating member 20 at its proximal end. The one or more further electrodes are not activated when the penetrating member is retracted and only become active when the penetrating member has exited the catheter. Once activated, these one or more further electrodes form an asymmetric electric field. This allows for fine adjustment of the alignment of the penetrating member as it is crosses to ensure that it remains on target. Furthermore, in this configuration, the sensing catheter 100 will detect when the penetrating member has successfully penetrated into the vein based on several different measurements including amplitude and conductance.

In FIG. 3a a penetrating member 20 is shown that has a positive ring electrode 39 and a negative ring electrode 41 on its distal tip. The electrodes 39, 41 together generate a spatially variant or asymmetric electric field. The sensing electrodes 108, 110 on the sensing catheter 100 measures the dipole electric field created by the two source electrodes 39, 41. As the penetrating member 20 approaches the sensing catheter 100 the measured signal will reach a maximum when the tip of the penetrating member 20 is nearest the sensing electrode 100. If the penetrating member 20 advances beyond (i.e. overshoots) the sensing catheter 100 the signal will start to decrease. As an alternative, the sensing electrodes 108, 110 can be located on the penetrating member 20 and the source electrodes 39, 41 are on the sensing catheter 100. This functionality can be accomplished electronically or using software to configure the apparatus accordingly.

FIG. 3b shows an alternative example of the penetrating member 20 shown in FIG. 3a; this example having two pairs of source electrodes 39, 41 on its distal end. Each pair of source electrodes 39, 41 are arranged in a diametrically opposed fashion on a circumference of the penetrating member 20; the first pair of electrodes 39, 41 angularly displaced by approximately 90° from the other pair of electrodes. This is best shown in FIG. 3c which is a cross-sectional view of the penetration member 20 at the position of the electrode pairs.

Each pair of electrodes creates a dipole electric field with a zero value along a plane that lies equidistant between them when the electrodes are activated. In this arrangement the signal measured by the electrodes 108, 110 on the sensing catheter 100 will vary with movement of the penetrating member 20 in the x-y plane (i.e. along or across the longitudinal axis L of the sensing catheter 100; as shown in FIG. 3c). A measured value of 0V when both pairs of electrodes are active indicates that the penetrating member 20 is aligned with the positive sensing catheter electrode 108. A value greater than 0V indicates a degree of misalignment. The amplitude of signal is indicative of alignment with values closer to null (0V) indicating greater alignment.

This example need not be limited to having two pairs of electrodes. Similar functionality may be achieved with three or more pairs of electrodes, for example, 4 pairs or 8 pairs (i.e. quadropole or octopole), or more pairs of electrodes on the penetration member 20.

FIG. 3d shows another example of a penetrating member 20 having one or more electrodes. In this example, the penetrating member 20 has a single ring source electrode 45 that forms the tip of the penetrating member 20. When the penetrating member is formed of a conducting material, such as metal, this configuration requires insulating material 47 to separate the electrode 45 that forms the tip of the penetration member 20 and the remainder of the penetration member 20. A wire 49 connects the electrode 45 to a power source. In use, current is applied to the source electrode 45 and a voltage is measured on the sensing electrode 108 relative to the ground signal measured from the grounding electrode 110 on the sensing catheter 100. In an alternative example the electrode 45 acts as voltage source and the current is measured at electrode 108. The current or voltage measured by the electrode 108 on the sensing catheter 100 will increase when the tip of the penetrating member 20 is nearest the sensing electrode 108 and will be at a maximum if the penetrating member 20 contacts the sensing electrode 108. A high or maximum signal may be used to indicate that the penetrating member has successfully entered the vessel.

FIG. 3e shows an alternative example where the entire penetrating member 20 acts as the source electrode 45 and functions as described above.

In a further example, a penetration member 20 with electrodes 39, 41 or 45 on its distal end form part of a catheter that does not itself comprise radial alignment electrodes. In this example, the electrodes on the penetration member 20 may be used for radial alignment prior to deployment of the penetration member 20. Alternatively, there may be no radial alignment of the catheter prior to deployment of the penetration member 20. In this example, the direction of the penetration member 20 is monitored by the signal generated in the sensing catheter 100 by the electric field created by electrodes 39, 41 or 45 on the penetration member 20.

In the prior art apparatus comprising the two catheters 10, 100 are connected to an electronic alignment monitor system 200. The electronic alignment monitor system 200 applies a voltage to the distal electrodes 22, 24 of the source catheter 10. In one example voltage is applied to spatially opposite electrodes. The voltage applied is preferably an AC voltage. Suitably, the voltage may alternate with a frequency of between 10 Hz and 1 MHZ, more suitably the voltage may alternate at a frequency of between 1 kHz and 100 kHz. Typically, the amplitude of the voltage may be between 1 mV to 10 V. Suitably, the current has to be within the limits set by EN60601-1. The electronic alignment system 200 may also display the alignment signal.

It is known that alignment of the catheters 10, 100 may be based on the measurement by the sensing catheter 100 of an asymmetrical electric field generated by the source catheter 10. An electric potential field measured by the sensing electrode 108 will be greatest when the positive electrode 22 on the source catheter is perfectly aligned with the center of the sensing electrode 108. The minimum voltage measurement will occur when the negative electrode 24 is aligned with the center of the sensing electrode 108. The sensing electrode 108 is in the form of a ring, so its measurements are independent of any rotation of the sensing catheter 100. In essence, the sensing electrode 108 is an omni-spatially variant receiver of the electrical signal (or absence of signal) generated by the source catheter 10. Therefore, if the opening 19 is in line with the positive source electrode 22 it is possible to align its trajectory with the target vessel or cavity that it needs to pierce by rotating the source catheter 10 until the peak voltage is detected by the sensing electrode 108. Alternatively the minimum or null signal can be used for alignment.

Alignment Processing System

In a first aspect the invention provides an apparatus for determining alignment between a source device and a target device. The apparatus comprises the source device, the target device, and a processing system.

Figure 5:
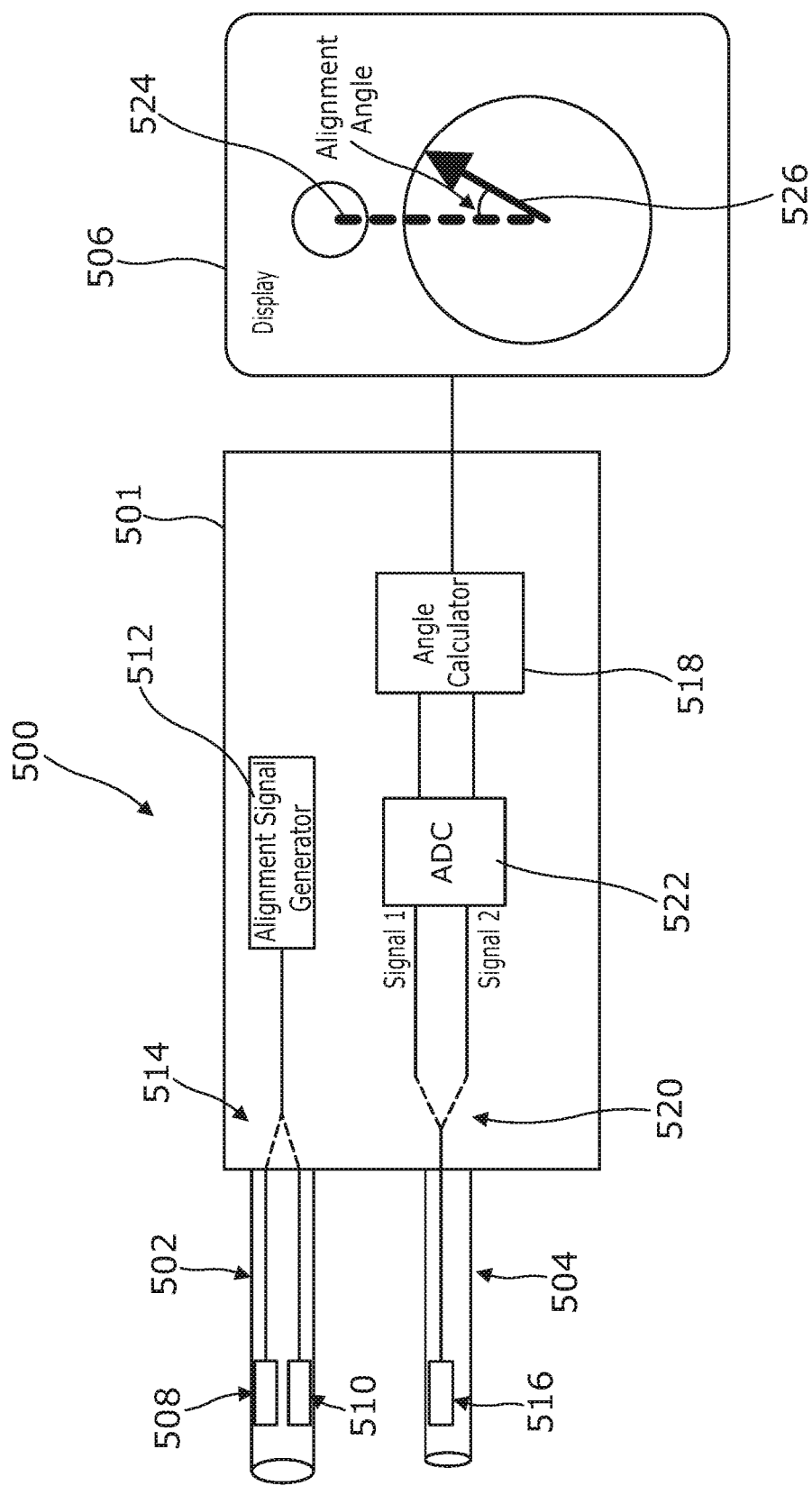
FIG. 5 is a block diagram showing a specific embodiment of an alignment processing system being used with the apparatus shown in FIGS. 1, 2 4a and 4b.

An embodiment of an apparatus 500 including an alignment processing system 501 in accordance with the present invention is shown in FIG. 5. While not limited to any particular use, the processing system 501 may be used in the electronic alignment monitor system 200 of the prior art apparatus described above. In the embodiment of an apparatus 500 including an alignment processing system 501 shown in FIG. 5, a source catheter 502, a target catheter 504 and a display 506 are also depicted.

In the embodiment of FIG. 5, a first spatially variant (or directional or asymmetric) field generator 508 and a second spatially variant (or directional or asymmetric) field generator 510 are mounted on the source catheter 502. In other embodiments, more than two spatially variant (or directional or asymmetric) field generators may be provided on the source catheter 502.

Spatially variant field generators are, for example, one or more pairs of electrodes configured to create dipoles, quadrupoles, octopoles etc. between the electrodes. Other generators that create spatially variant (or directional or asymmetric fields) that fall within the definition provided herein may also be used.

Each field generator 508, 510 produces a spatially variant field or signal. Suitably, this field has a known angular dependence. The angular dependence of each of the first spatially variant field and the second spatially variant field are angularly offset around a shared or common axis or otherwise.

The processing system 501 comprises an alignment signal generator 512. The alignment signal generator 512 is connected to the source catheter 502. The connection may be by appropriate wiring or via wireless communication. The processing system 501 directs the alignment signal either to the first spatially variant field generator 508 or to the second spatially variant field generator 510 mounted on the source catheter 502. The direction of the signals may be via a first switch arrangement 514. Each spatially variant field generator 508, 510 produces a spatially variant field or signal with a known angular dependence. The two angular dependences may be the same or different, suitably they are the same. The first and second spatially variant fields are angularly offset from each other.

In one embodiment, the spatially variant field generators 508, 510 have the same or similar angular dependence but one is angularly displaced from the other, for example the spatially variant field generators are displaced by 90 degrees around a common axis, for example, the longitudinal axis of the source catheter 502, such that the generators 508, 510 are mounted orthogonally. In other words, the spatially variant field generators 508, 510 may be configured to produce the same or similar type of field, e.g. a dipole or a quadropole, but the fields generated are differently arranged, so that rotational movement of the source catheter 502 relative to a sensor results in a different reading at the target catheter 504 in terms of signal amplitude and/or polarity for each field as it is switched.

The above generally describes a set of dipole fields that are spatially variant according to a sinusoidal (sin or cos) waveform.

Alternatively, the processing system 501 can activate both, or two or more, pairs of electrodes at the same time using different carrier frequencies or rapidly switch between each electrode pair in order to get both measurements at the same time.

The electric field may be any suitable electric field. Typically, the electric field is generated using supplied direct current (DC) or alternating current (AC). Suitably, the signals supplied to the electrodes are AC signals. In these embodiments, peak to peak values for voltage amplitude may be measured for AC signals. The phase of the sensed signal is also measured and compared to the phase of the voltage applied to the positive electrode of the source catheter. In this way, a sign can be given to the peak to peak value, and a useable value for alignment can be achieved. If the signal is in phase, the sign is positive, and if the signal is 180 degrees out of phase, the sign is negative. In this way it is possible to distinguish between the otherwise identical peak-to-peak amplitudes detected when the source device is optimally aligned (in phase at the detector and provided with a positive sign) and when it is rotated 180 degrees from optimal alignment (out of phase at the detector and provided with a negative sign).

A sensor 516 mounted on the target catheter 504 detects the spatially variant field or signal generated by the source catheter 502. The sensor 516 detects the first spatially variant signal or the second spatially variant signal depending on which spatially variant field generator 508, 510 is being driven as determined by the first switch arrangement 514 and the alignment signal generator 512. The sensor 516 is connected to a processor (an angle calculator) 518 via a second switch arrangement 520 and an analog-to-digital converter (ADC) 522. The second switch arrangement 520 may be a hardware or software switch arrangement. The second switch arrangement 520 diverts the detected spatially variant signal sensed at the sensor 516 to one of two memory locations (not shown). The processor 518 calculates the alignment angle based on the received spatially variant signal and the type of spatially variant signal. The second switch 520 is controlled to divert the received spatially variant signal to a first memory location of the two memory locations if the first switch arrangement 514 is causing the first spatially variant signal generator 508 to generate the first spatially variant signal, and to a second memory location of the two memory locations if the first switch arrangement 514 is causing the second spatially variant signal generator 510 to generate the second spatially variant signal. The first switch arrangement 514 and second switch arrangement 520 are therefore linked in some respect, so that switching of the first switch arrangement 514 is copied in the second switch arrangement 520 so that the correct memory location is selected for the spatially variant signal being generated.

Instead of or as well as a switching arrangement 514 as described above, each spatially variant field generator 508, 510 may be supplied with a signal having a distinct carrier frequency. In other words, the first spatially variant field generator 508 may be provided with a first spatially variant signal having a first frequency, and, at the same time or otherwise, the second spatially variant field generator 510 may be provided with a second spatially variant signal having a second frequency. In this embodiment, the sensor 516 is configured to detect both signals, and the processor 518 incorporates hardware and/or software configured to separate the signals from one another based on frequency. For example, a band pass filter or filters may be used to separate the signals. Alternatively or additionally, a multiplexer arrangement may be used to generate time-dependent signals for transmission to each electrode. Similarly, to calculate the alignment angle, the processor 518 has some link indicating which spatially variant signal is which.

In an embodiment, the alignment angle is calculated as a function of the two direction signals:

alignment angle=function(first spatially variant signal, second spatially variant signal).

In other words, the alignment angle is calculated using a function to which the spatially variant signals are inputs. In embodiments, by spatially variant signal as input, it is meant that an amplitude or value of the spatially variant signal is used.

Once the alignment angle has been calculated by the processor 518 according to this function, it may be subsequently displayed on a display 506. The alignment angle may be displayed in any suitable manner. For example the alignment angle may be displayed as an arrow on a clock face or similar circular indicator, where the arrow is displayed at the alignment angle away from a reference mark. The reference mark is arranged to define a direction where the source and target catheters are in a pre-defined and desired orientation relative to one another. The desired orientation may be such that the catheters are so aligned that ejection of the needle/penetration member is from the source catheter towards or directly towards the target catheter. The arrow may display the measured orientation as given by the alignment angle calculation.

In the example shown in FIG. 5, the reference mark 524 is a vertical line and so the direction is displayed as an arrow 526 at an angle away from the vertical. In use, the operator typically uses this display 506 to rotate the source catheter 502 until the alignment arrow 526 is aligned with the reference mark 524, which will mean the orientation of the catheter 502 is such that a penetrating member such as a needle ejected from the source catheter 502 will be directed towards the target catheter 504.

The advantage of this calculation and display of the alignment angle is that it is clear to the operator which direction to rotate the source catheter 502 to attain alignment, and once the alignment angle is in the desired orientation, no further rotation is required, unlike the situation where a maximum signal is sought.

In one embodiment, the spatially variant signal generators 508, 510 are displaced by 90° from one another. Each spatially variant signal generator 508, 510 produces a spatially variant signal with sinusoidal angular dependence. In this embodiment the calculation of the alignment is with the equation:

alignment angle=Offset+arctan(first spatially variant signal, second spatially variant signal).

In other words, the alignment angle is an offset angle added to the inverse tangent function where the first spatially variant signal and the second spatially variant signal are inputs. The notation arctan (x,y) refers to the inverse tangent function with two input arguments, x and y, which in this case are the measured values of the first spatially variant signal and the second spatially variant signal respectively. Again here, in embodiments, the first spatially variant signal and the second spatially variant signal voltage amplitudes are used as input arguments.

In this equation the term 'offset' refers to where an angle of optimal signal is offset from the alignment required for the device, for example if a penetrating member does not exit from the source device in line with the spatially variant field. This effectively normalises the alignment as indicated by the detected signals for any requirements of the specific device.

Figure 6:
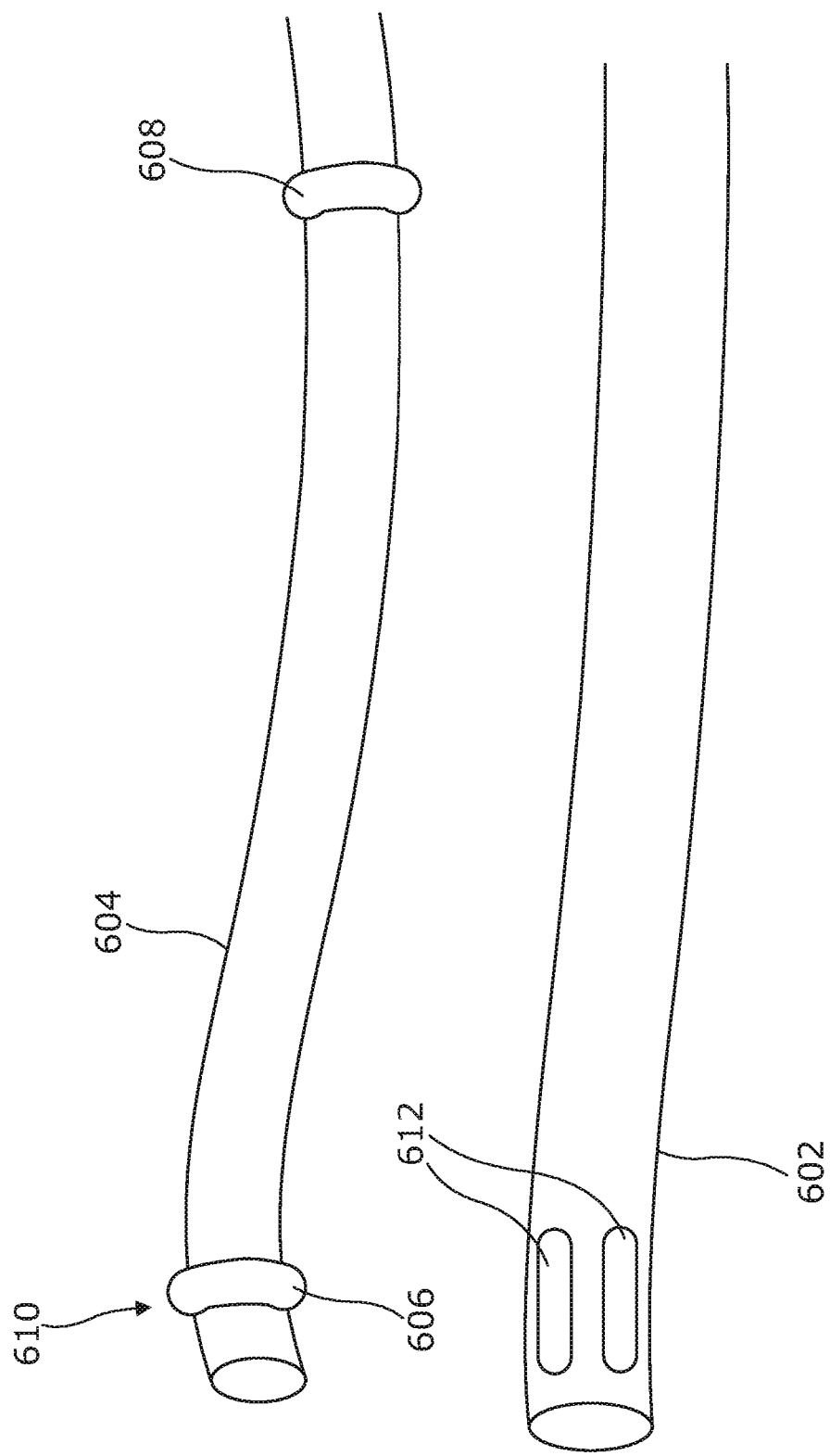
FIG. 6 is a representation of an embodiment of the apparatus for use with the alignment processing system shown in FIG. 3.

In an embodiment of this approach the source catheter (or transmit catheter) can produce two separate circularly asymmetric electric fields and the target catheter (or receive catheter) detects the electric field. As illustrated in FIG. 6, which shows a source catheter 602 and a target catheter 604 according to this embodiment, two ring electrodes 606, 608 are mounted on the target catheter 604. One of the two ring electrodes 608 acts as a reference electrode and is positioned some distance away from the alignment plane, and the other of the two ring electrodes 606 is a signal electrode that is positioned at the distal end 610 of the target catheter 604 and is arranged to be positioned adjacent to transmit electrodes 612 of the source catheter 602.

In FIG. 6, four strip electrodes 612, only two of which are visible in FIG. 6, are mounted on the source catheter 602 and are placed in diametrically opposed pairs around the circumference of the source catheter 602 so that each electrode 612 is orthogonal to its two neighbouring electrodes 612.

Figure 7A:
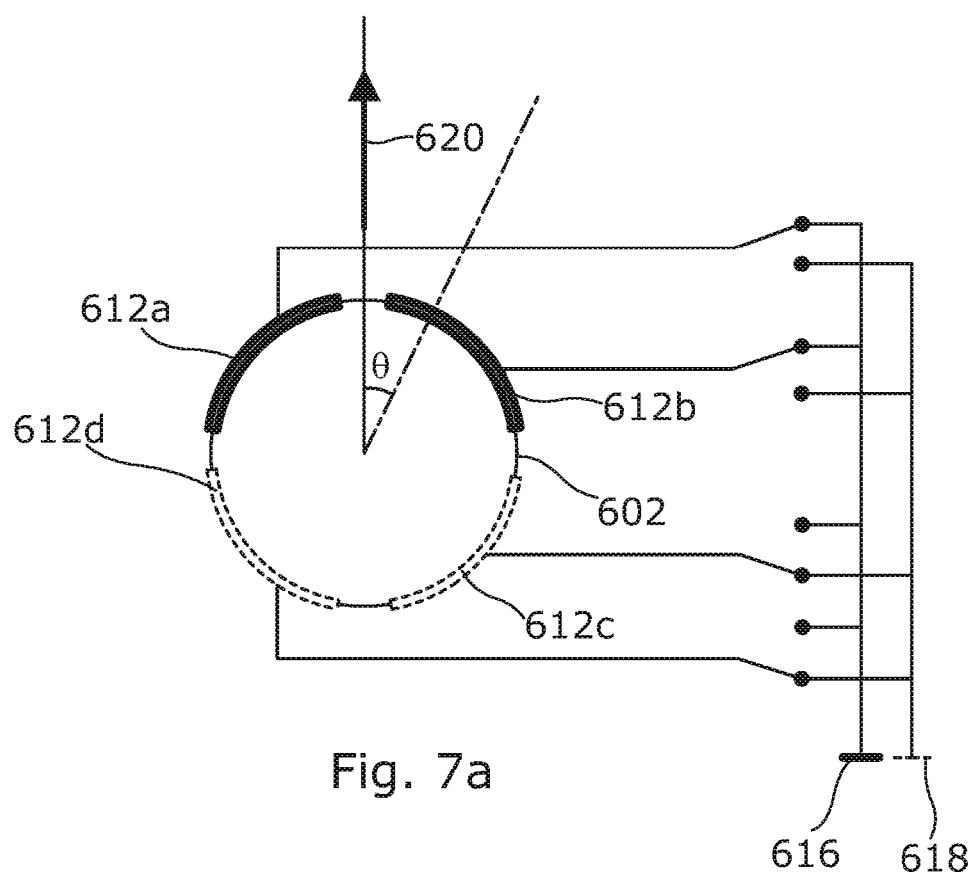
FIGS. 7a and 7b are alternate representations of switched electrode arrangements for the source catheter when the processing system is switched to a first mode.
Figure 9A:
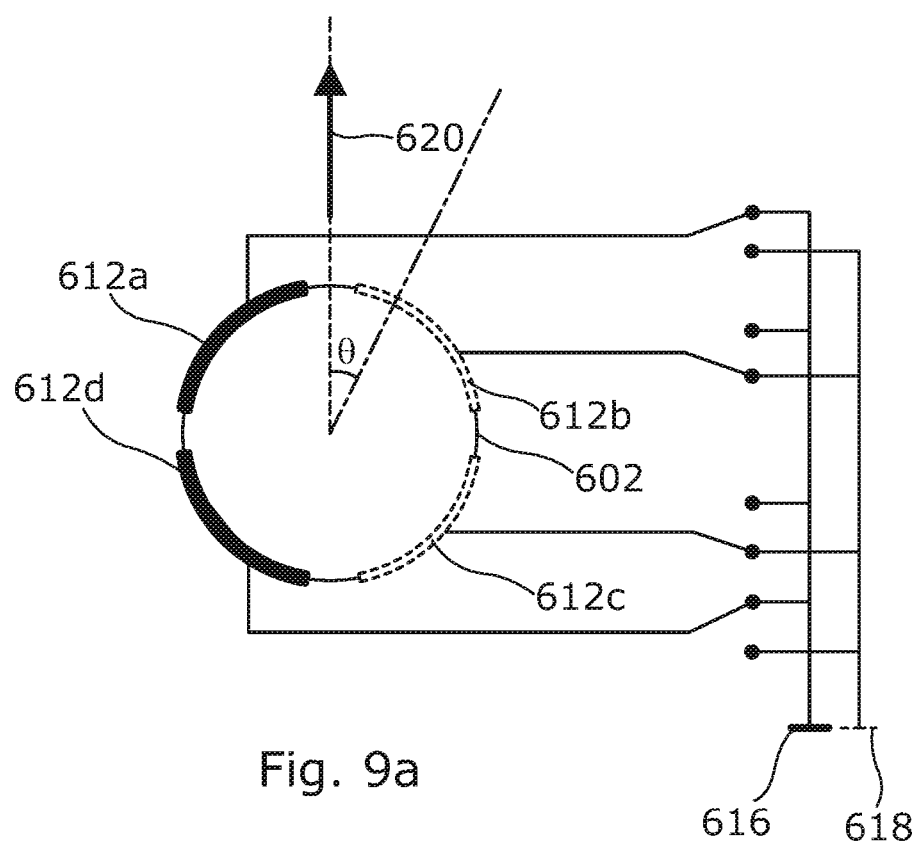
FIGS. 9a and 9b are alternate representations of switched electrode arrangements for the source catheter when the processing system is switched to a second mode.
Figure 9B:
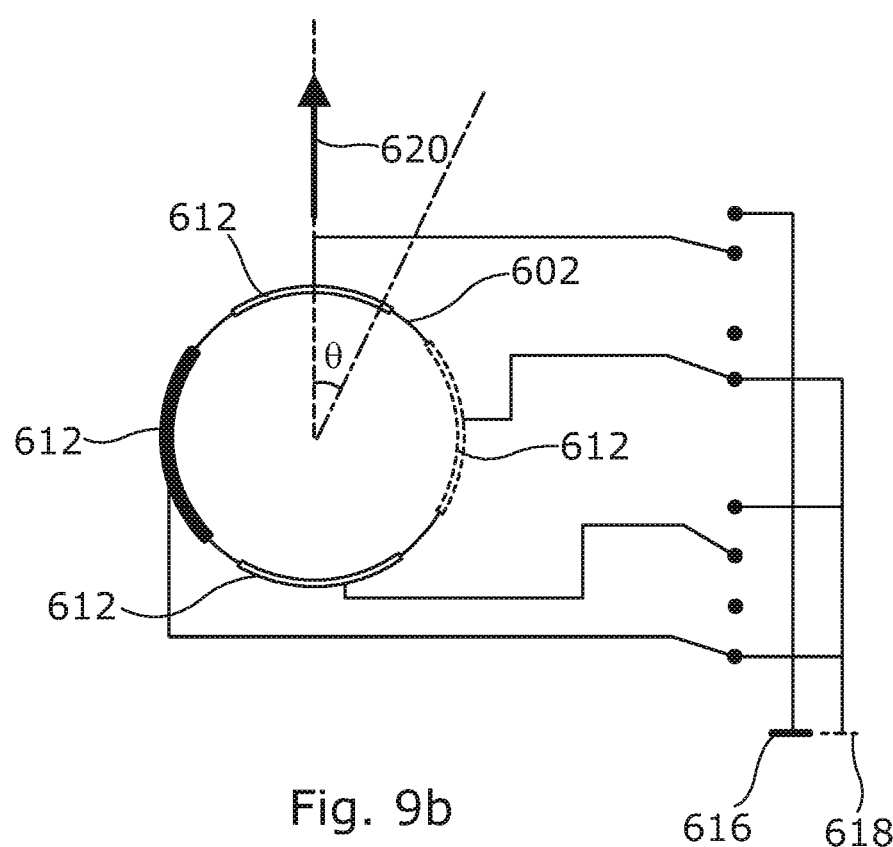

As can be seen from FIGS. 7a and 9a, the electrodes 612, here referred to as 612a to 612d where 612a and 612d are upper and lower electrodes to the left of an alignment direction 620 as drawn; and 612b and 612c are upper and lower electrodes to the right of the alignment direction 620 as drawn, are connected via programmable switches (not shown), here forming the first switch arrangement 514, to the two poles 616, 618 of the alignment signal generator 512 and aligned relative to a needle/penetration member exit direction, here indicated by an arrow 620.

Figure 7B:
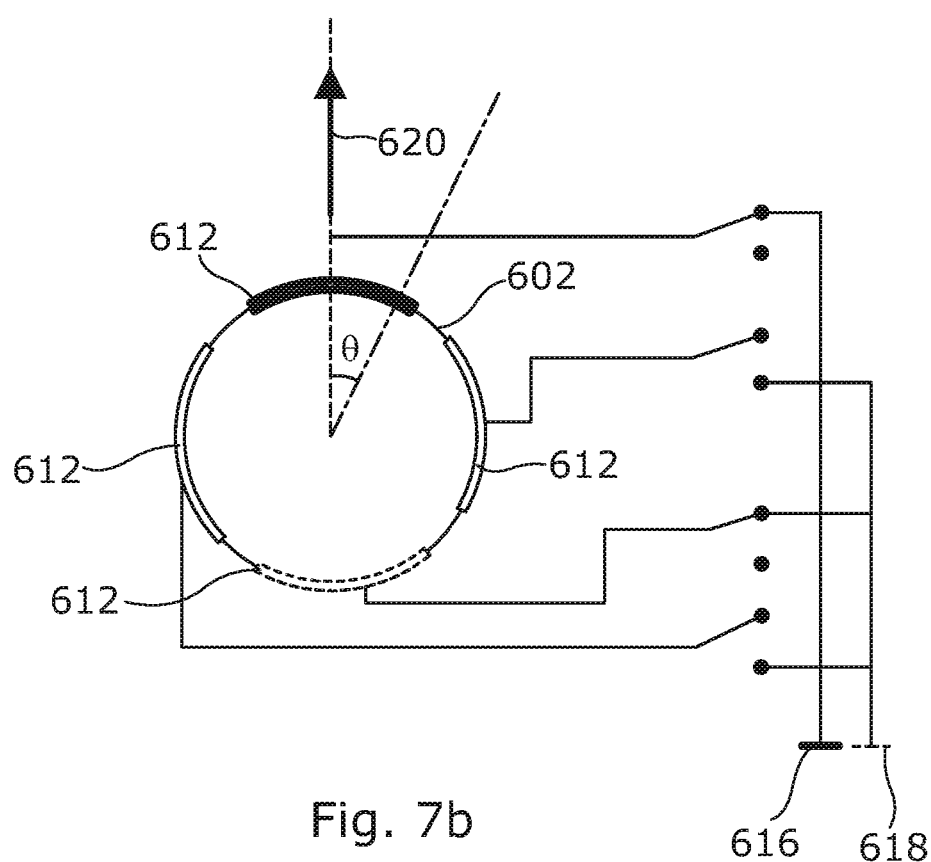
Figure 8:
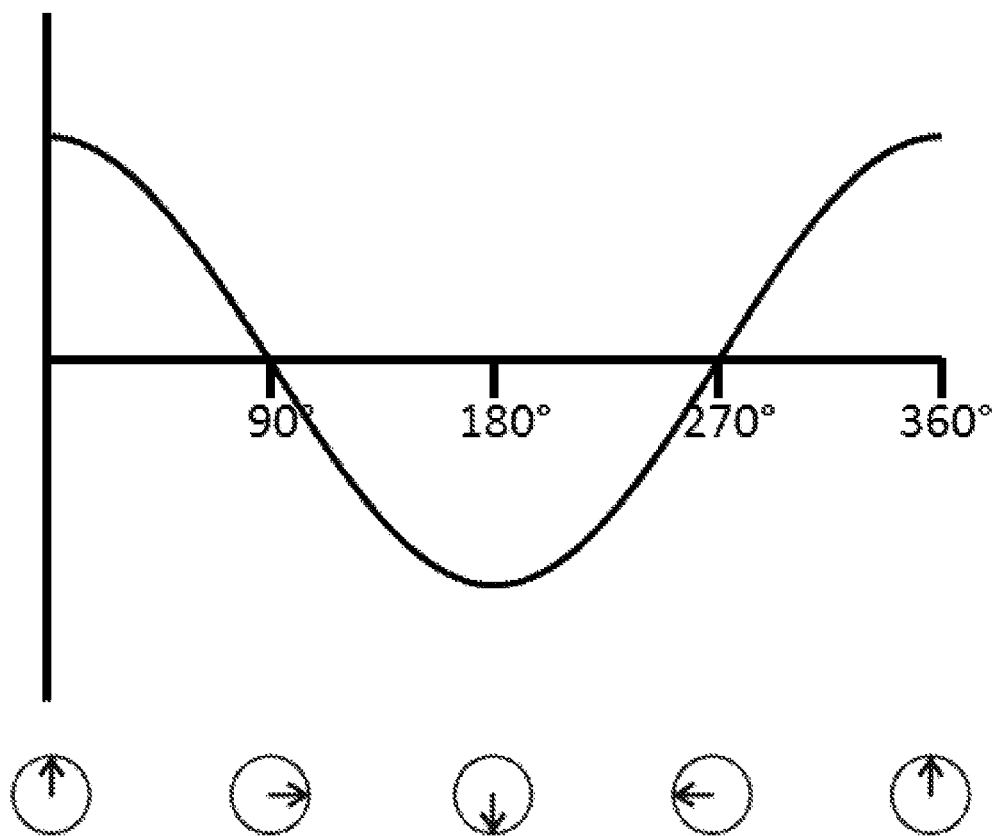
FIG. 8 is a diagram indicating the signal output of the source catheter versus rotation angle of the source catheter relative to the sensing catheter, when the system shown in either

According to the present embodiment, the electrodes 612, also referred to as transmit electrodes, of the source catheter 602 are operable in two modes to generate the two spatially variant fields. In the embodiments shown in FIGS. 7a and 7b, in a first mode of the two modes, i.e. Mode 1, the electrodes 612 are connected together in front and back mode relative to the alignment direction shown by the arrow. In the embodiment of FIG. 7a, this means that the upper electrodes 612a and 612b are connected to one pole 616 and the lower electrodes 612d and 612c are connected to the other pole 618. This gives a maximum signal when needle/penetration member exit direction 620 (known as the alignment direction) on the source catheter 602 is pointing towards the target catheter 604. In the plot of signal amplitude versus angle shown in FIG. 8, the positive values are when the measured AC signal is in-phase, and the negative values are when the measured AC signal is out of phase relative to the AC signal applied to the electrode(s).

This mode gives an unambiguous signal maximum for alignment, but the signal is not very sensitive to small deflections off-axis. To improve angular sensitivity, a second mode of the two modes, i.e. Mode 2, is implemented, where the electrodes are connected in a side-side configuration as illustrated in FIG. 9a. In the arrangement of FIG. 9a, this means that the left electrodes 612a, 612d are connected to one pole 616, while the right electrodes 612b, 612c are connected to the other pole 618.

Figure 10:
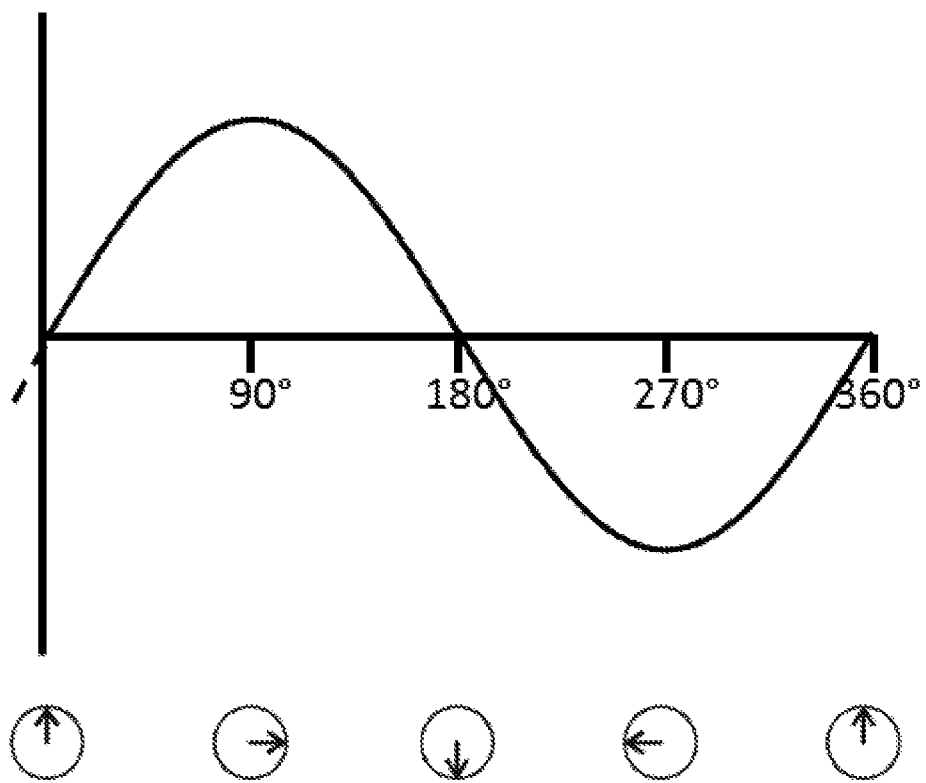
FIG. 10 is a diagram indicating the signal output of the sensing catheter versus angle of the source catheter relative to the sensing catheter, when the system shown in FIG. 9a or 9b is switched to the second mode.

In this second mode, the source catheter 602 is aligned with the target catheter 604 when the signal is zero, as can be seen in FIG. 10. However there is ambiguity in that there is also a zero at 180°. For this reason both modes are needed, Mode 1 to align, and Mode 2 for fine tuning summarised in FIG. 11. This way, the processing system 501 is able to distinguish the zero at 180° in Mode 2 as being when the source catheter 602 is anti-aligned because of the negative value measured in Mode 1 in this alignment.

The two signals can be used to calculate the alignment angle using the equation:

$$\text{alignment angle} = \arctan(\text{Mode1}, \text{Mode2}).$$

Figure 11:
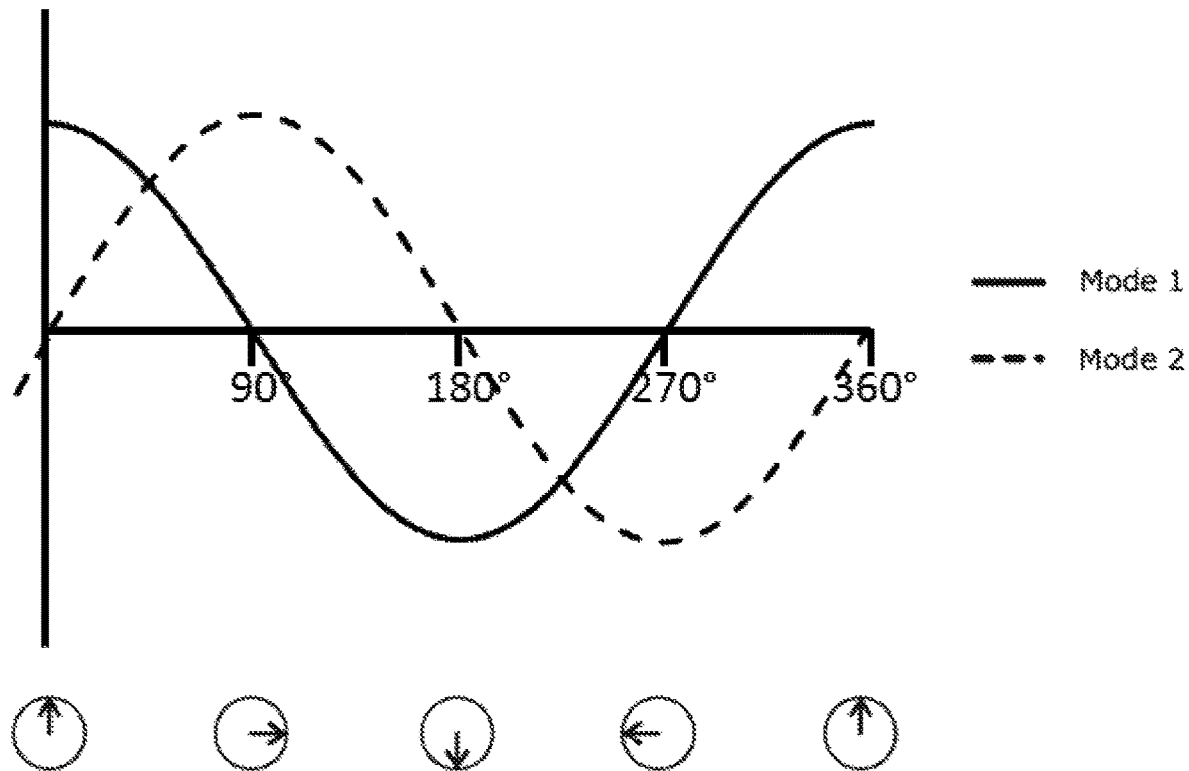
FIG. 11 is a diagram in which the diagrams of FIGS. 8 and 10 are overlaid, illustrating the signal output of the sensing catheter versus angle of the source catheter relative to the sensing catheter, when the system is switched between the first and second modes.

In this embodiment, the offset is zero so is not included in the equation. In embodiments, the voltage amplitudes measured when the source catheter 602 is operated in the given mode is used as the corresponding input. For example, as can be seen in FIG. 11, the alignment angle is 0 when the measured voltage amplitude in Mode 1 is 1, and when the voltage amplitude in Mode 2 is 0. Arctan (1,0) is 0 degrees, so the catheters 602, 604 are aligned.

Considering this embodiment in terms of the general embodiment described in relation to FIG. 5, the four strip electrodes 612 of the source catheter 602 operate as both the first and second spatially variant (or directional or asymmetric) field generators 508, 510. A single spatially variant (or directional or asymmetric) field generator can be considered to be the first spatially variant (or directional or asymmetric) field generator 508 and the second spatially variant (or directional or asymmetric) field generator 510 by virtue of the fact that it is able to generate a first spatially variant (or directional or asymmetric) field and a second spatially variant (or directional or asymmetric) field at different times when driven in different configurations by the first switch arrangement 514.

In general operation of the above embodiments, it is assumed the first switch arrangement 514 is programmed to switch between the first and second spatially variant field generators 508, 510 at regular intervals so that the alignment angle can be calculated as the function of the two modes as described.

In one embodiment, the first mode may be implemented until an approximate alignment is achieved, and when the approximate alignment is achieved, the second mode may subsequently be used to effectively 'fine tune' the alignment. The first mode, where a peak is used for alignment, lends itself to approximate alignment because the signal is insensitive to small deflections off-axis due to the peak having a wider coverage than other parts of the signal. The second mode, where a zero is used for alignment, lends itself to fine-tuning because the zero of the signal is at the point having the highest gradient, so minor changes cause variation from zero and the signal is sensitive to small deflections.

In alternative embodiments, the system can activate more than one set of electrodes, or all electrodes, at the same time using different carrier frequencies or rapidly switch between each electrode pair in order to get both, or all, measurements at the same time as described in detail above.

In another embodiment of this approach, the source catheter houses two orthogonal coils that each generate a magnetic field when connected to an alternating current source. One or more receive coils are mounted on the target catheter that each produce a signal proportional to the amplitude of the magnetic field generated by the source catheter. The amplitude of the magnetic field will depend on the alignment angle and so the alignment angle can be calculated as previously described.

Self-Centring of Catheter

In a further aspect of the present invention, a target device is provided comprising a self-centring mechanism (SCM) for positioning the alignment centre of the target device towards or at the centre of a target lumen in which it is located.

Figure 12:
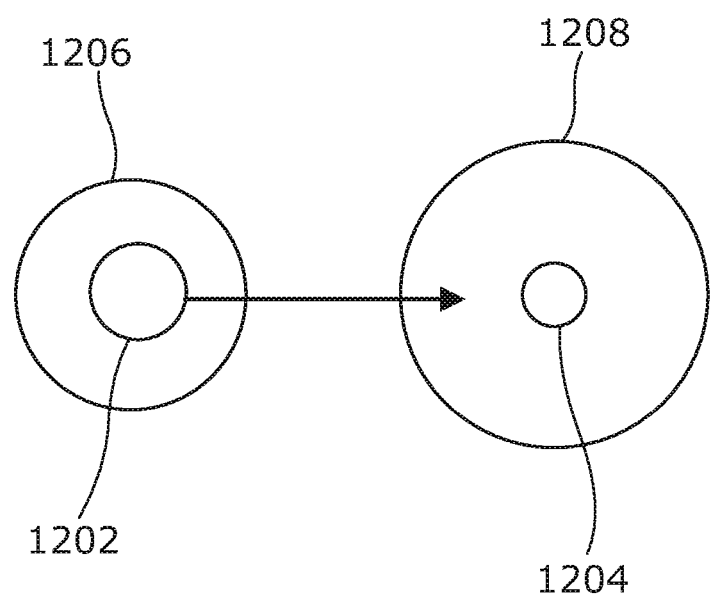
FIG. 12 is a representation illustrating a launch or source catheter in a launch lumen aligned with a target catheter in a target lumen, and the launch catheter being aligned to the centre of the target lumen.

Initially referring to FIG. 12, in an embodiment, a launch catheter (i.e. source catheter) 1202 located in a launch or source lumen 1206 is rotationally aligned to a target catheter 1204, located in a target lumen 1208. The target catheter 1204 can have multiple properties/uses. Its primary purpose is to serve as a platform for one or more sensing electrodes that measure the asymmetric electric field generated by the launch catheter 1202 which enables a processing system (not shown) to calculate an angle of alignment between the launch catheter 1202 and the target catheter 1204. Under the assumption that the target catheter 1204 is centred within the target lumen 1208, the launch catheter 1202 would also be aligned to the centre of the target lumen 1208 when the launch catheter 1202 is aligned to the target catheter 1204, as shown in FIG. 12.

To ensure free passage of the target catheter 1204 in the target lumen 1208, it is advantageous that the target catheter 1204 has a smaller diameter than the lumen 1208 in which it is located. This however means that the distal end of the target catheter 1204 may not be positioned in the centre of the lumen 1208. As alignment is to the target catheter 1204, then this can result in the source catheter 1202 aligning to the edge or side of the target lumen 1208 increasing the potential for missing the target lumen 1208, or penetrating the target lumen 1208 close to the side which increases the risk of dissecting the target lumen 1208 or the penetrating member exiting the target lumen 1208 on the opposite side. Positioning of the centre of alignment of the target catheter 1204 in or towards the centre of the target lumen 1208 is therefore desirable.

The target catheter 1204 may therefore suitably comprise a self-centring mechanism (SCM) that positions the alignment centre of the target catheter 1204 towards or at the centre of the target lumen 1208. Any configuration for the SCM that effectively positions the centre of alignment of the target catheter 1204 towards or at the centre of the target lumen 1208 is encompassed by the present invention, Suitably, the SCM comprises one or more radially expanding members. The SCM may employ rib-like expandable members that extend radially in an arcuate manner as shown in FIGS. 13 to 18g and described below. The SCM may alternatively, or in combination, comprise a braided or weaved pattern similar to knowns stents or occlusion devices.

In one embodiment of this aspect of the present invention, shown in FIGS. 13 to 18g, the SCM 1210 comprises one or more radially expandable members 1212. Suitably, the SCM 1210 comprises two or more radially expandable members 1212. Suitably, the radially expandable members are of substantially equal stiffness. Suitably, the radially expandable members are arranged in a substantially rotationally symmetrical orientation, which when deployed in a lumen 1208 or vessel or cavity, serve to centre the target catheter 1204. In one embodiment, the SCM 1210 is substantially similar to an endovascular or urinary snare, a clot catching basket, vessel occlusion plug, or self expanding stent.

Figure 13:
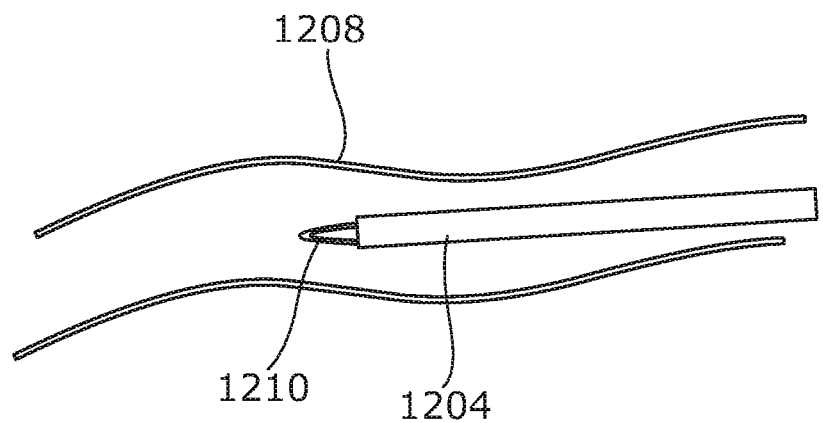
FIG. 13 is a representation illustrating an embodiment of a target catheter with a self-centring mechanism, where the self-centring mechanism is in a low radial profile retracted position within the target lumen.
Figure 14:
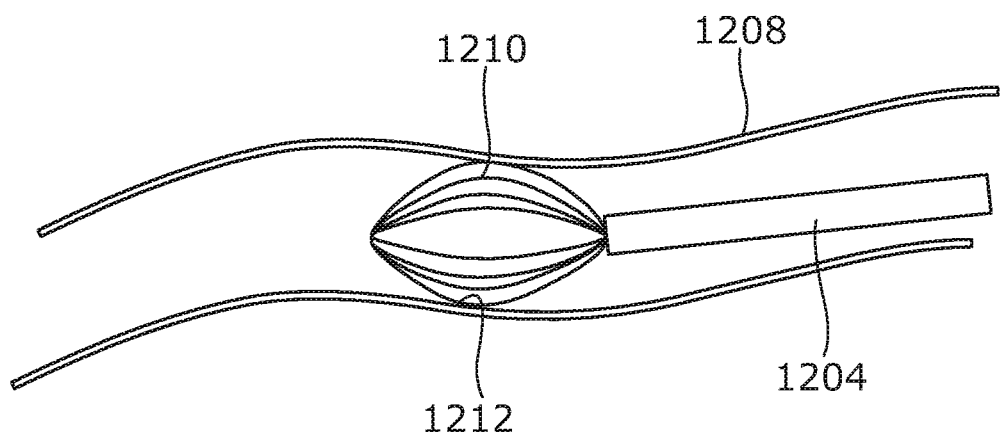
FIG. 14 is a representation illustrating an embodiment of the target catheter with the self-centring mechanism in an expanded configuration with radially-expandable elements deployed within the target lumen.
Figure 15:
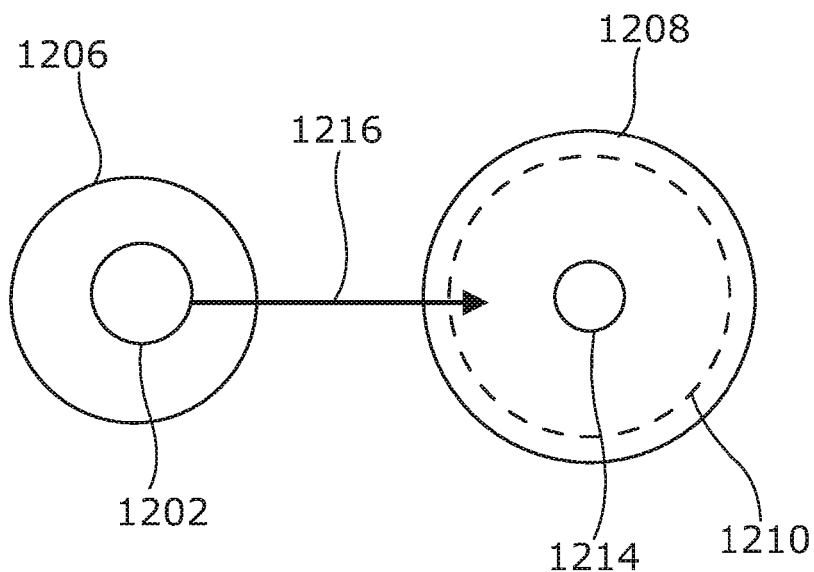
FIG. 15 is a representation illustrating an embodiment of a launch catheter and a target catheter located within a launch lumen and a target lumen respectively, the self-centring mechanism being in the expanded configuration and creating a target point source located centrally in the target lumen.

The SCM 1210 is configurable in a retracted configuration and an expanded configuration. In the retracted configuration, the SCM 1210 has a low radial profile and can be delivered down the vessel in the low radial profile, retracted configuration. Suitably, in the retracted configuration, the SCM 1210 is retracted at least partially, preferably fully, with a lumen on the target catheter 1204. Once the target catheter 1204 is correctly located, the SCM 1210 is deployed into the expanded configuration in a position that exerts pressure on the inner circumference of the vessel wall. Suitably deployment may be by movement of the SCM 1210 longitudinally from the open distal end of the target catheter. FIGS. 13 and 14 show the SCM 1210 in the target lumen 1208 in the retracted and expanded configuration respectively. Suitably, the SCM 1210 may comprise one or more expandable elements 1212 that are retracted within the lumen of the target catheter 1204 in the low radial profile configuration to be deployed from the end of the target catheter 1204 at the appropriate position to take the expanded configuration.

The SCM 1210 can be made out of any suitable material. Suitably, the SCM 1210 is made out of shape memory alloy, such as Nitinol™. In embodiments where the SCM 1210 is conductive and connected mechanically and electrically to a processing system, the members of the mechanism can be treated as a single sensing electrode located at the centre of the mechanism (target point source 1214, FIG. 15). This is in accordance with Gauss' law regarding the field from a symmetrical distribution of a charge around a sphere being equivalent to the field from a point charge at the centre of that sphere (http://physics.bu.edu/~duffy/semester2/d06_potential_spheres.html, accessed 17 Apr. 2019).

During the use of the electronic alignment or processing system, the SCM 1210 is opened to extend across the target lumen 1208. The advantage of using the SCM 1210 as the alignment electrode is that it is ensured to be at or close to the centre of the target lumen 1208. This in turn increases the potential accuracy of a penetrating member (PM) 1216 crossing from the launch lumen 1206 to the target lumen 1208.

Figure 16:
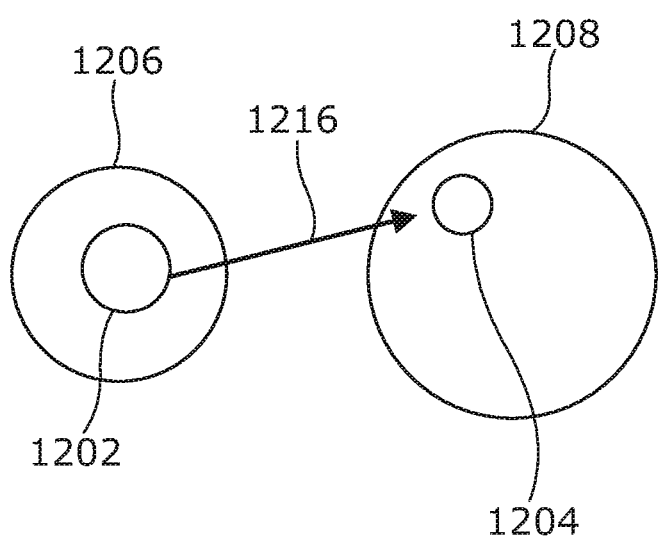
FIG. 16 is a representation illustrating the launch catheter and the target catheter in the launch lumen and the target lumen respectively, the target catheter not being in accordance with the present invention, or where the radially-expandable elements have not been deployed. The target point source formed by the target catheter is not fixed to the centre of the target lumen.

Without the SCM 1210, there is a risk of misalignment of the target catheter 1204 within the target lumen 1208 as shown in FIG. 16. Misalignment of the target catheter 1204 also risk misalignment of the PM 1216 to the target lumen 1208 because the target catheter 1204 is not centralized within the lumen 1208 and the alignment is achieved relative to the target catheter 1204.

Figure 17A:
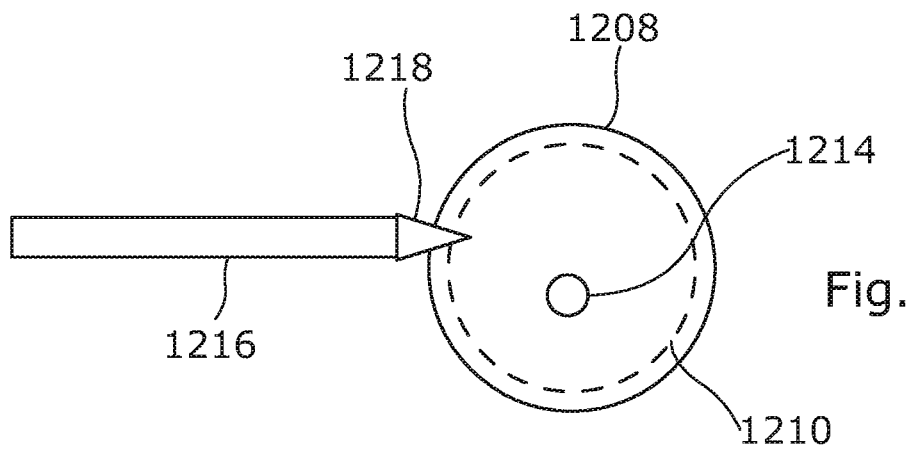
FIGS. 17a to 17c are representations of an embodiment of the present invention illustrating the progress of a penetrating member into the target lumen in which the target catheter is disposed with the self-centring mechanism in the expanded configuration and the target point source formed at or proximal to the centre thereof.
Figure 17B:
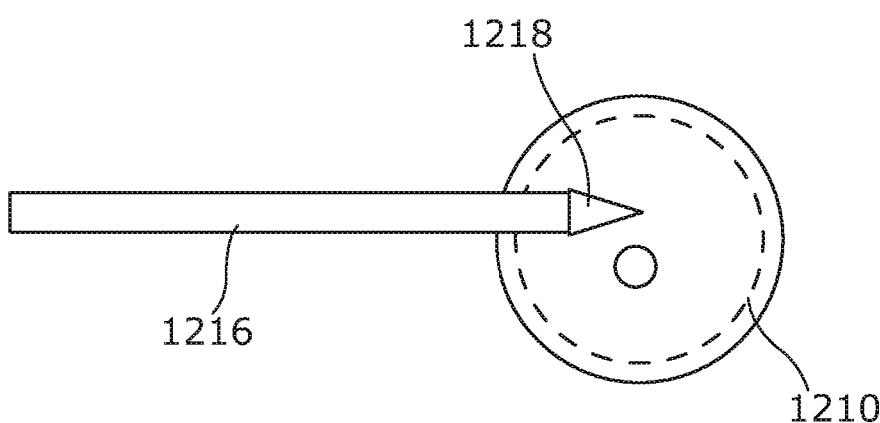
Figure 17C:
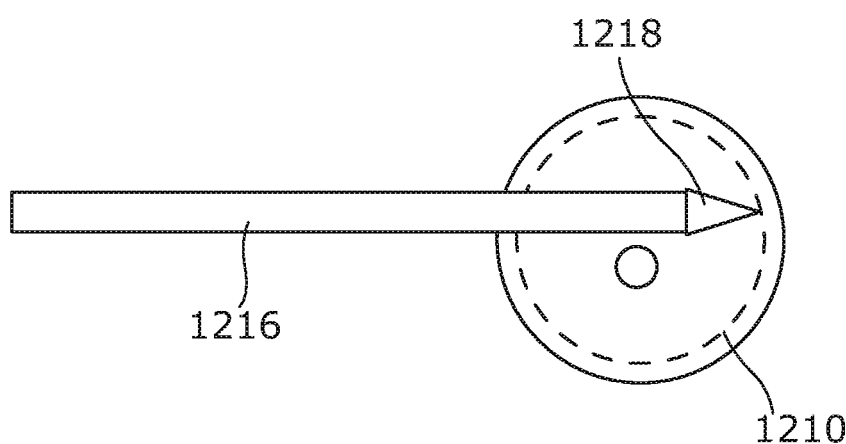
Figure 18:
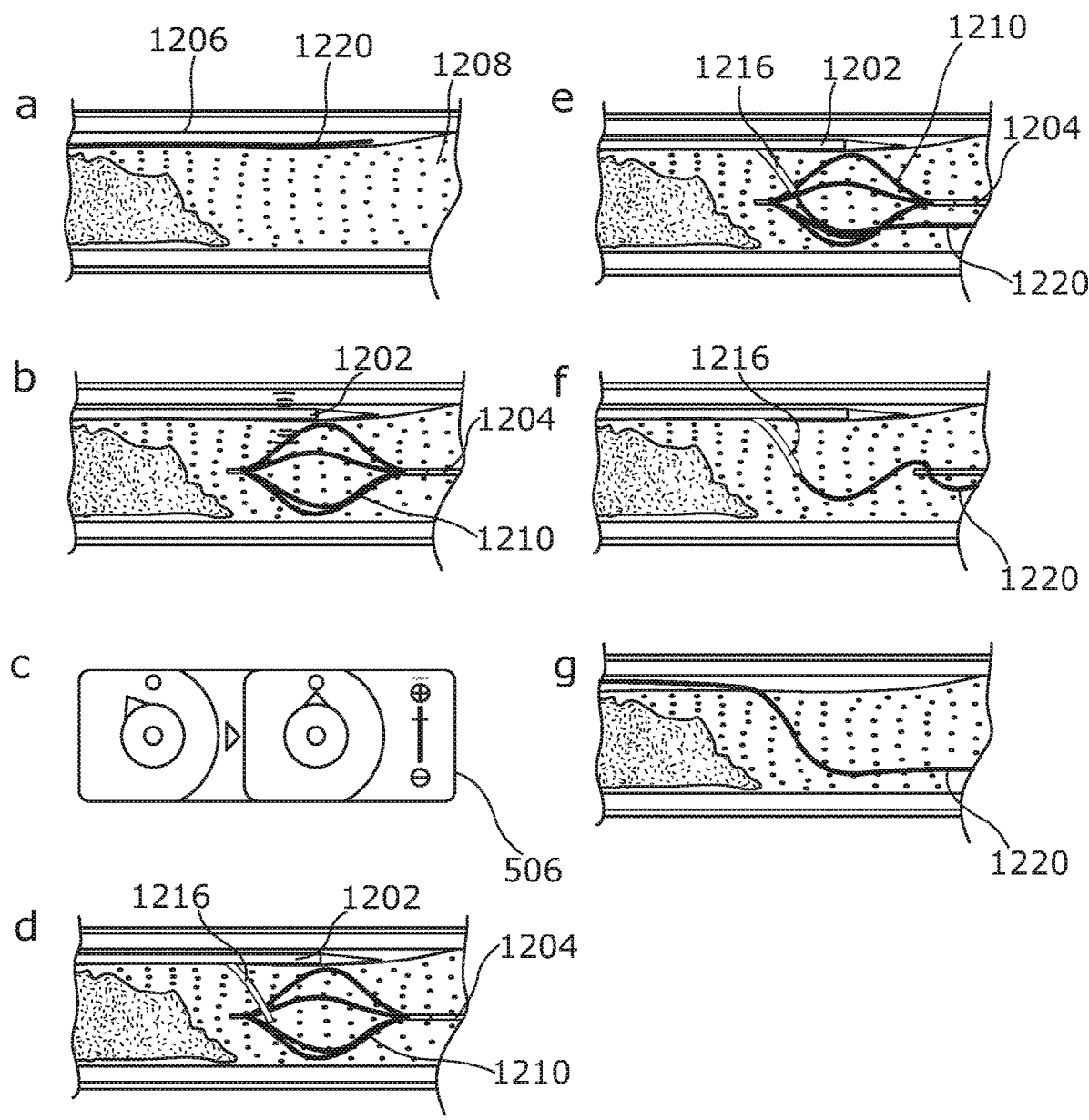
FIGS. 18a to 18g are a series of representations illustrating side views of an embodiment of the self-centring mechanism of the present invention, and processing system of the present invention deploying and capturing (snaring) a guide wire in the target lumen.

Additionally, as shown in FIGS. 17a to 17c, in an embodiment of the invention, the whole or part of the PM 1216 may be conductive. Suitably only the tip 1218 of the PM 1216 is conductive. When the SCM 1210, or a portion of the SCM 1210 is also conductive, and the members of the SCM 1210 are close enough together so that they make contact with the PM 1216 (such as in a Nitinol™ mesh or weave) then when the PM 1216 penetrates the target lumen 1208, it is possible to detect when the tip 1218 of the PM 1216 has entered the target lumen 1208, and furthermore whether it has passed or punctured out of the lumen 1208 again. This is very beneficial for the operator as it decreases the risk of puncturing through the lumen 1208 completely and causing excessive bleeding/damage. The electronic alignment system can detect contact being made by the PM 1216 to the SCM 1210 by taking various electrical measurements such as conductivity, resistivity or continuity between the PM 1216 and SCM 1210 or detecting changes in the electric field generated by the launch catheter 1202.

In use, the operator will detect a first contact between the PM 1216 and SCM 1210 when the PM 1216 first enters the lumen 1208, and this will be registered by the electronic alignment system, as in FIG. 17a. As in FIG. 17b, the operator can detect when the PM 1216 is safely in the lumen 1208 and there is not electrical contact between the tip 1218 of the PM 1216 and the SCM 1210. The operator can subsequently detect when the tip 1218 of the PM 1216 is close to the wall of the lumen 1208 again based on further measurements indicating contact between the PM 1216 and SCM 1210 because the PM 1216 will come into contact with the SCM 1210 again shortly before it has the potential to exit the lumen 1208, as shown in FIG. 17c.

Another advantage of using an SCM 1210 is that the application of radial force on the target lumen wall creates tension in the wall and reduces a potential deflection of the wall when pushed upon by the PM 1216 as it enters the target lumen 1208. In one embodiment, the SCM 1210 is comprised of Nitinol™ members that exert a radial force on the vessel wall similar to a self expanding metal stent. In this embodiment the radial force helps ensure a taut lumen wall which is easier to puncture through by the PM 1216.

As best shown in FIGS. 18a to 18g, in another embodiment of the invention, where a guidewire 1220 is passed from a launch lumen 1206 to a target lumen 1208, a further advantage of the SCM 1210 is its ability to be retracted when the guide wire 1220 has advanced partially into the target lumen 1208 as shown in FIGS. 18a to 18g. By retracting the SCM 1210 into the interior lumen of the target catheter 1204 when the guidewire 1220 has advanced partially into the target lumen 1208, the SCM 1210 acts as a snare, capturing and retaining the end of the guidewire 1220. This anchors the guidewire 1220 in position and facilitates the secure deployment of interventional devices into the target lumen 1208 along the guidewire 1220, or can be used to pull the guidewire 1220 further down the vessel. In FIG. 18a, a guide wire 1220 is positioned in the launch lumen 1206. In FIG. 18b, the launch catheter 1202 has been passed along the launch lumen 1206 over the guide wire 1220, and the target catheter 1204 is positioned within the target lumen 1208 with the SCM 1210 expanded. In FIG. 18c, the launch catheter 1202 and target catheter 1204 are aligned using the method described earlier in this document. Having aligned the two catheters 1202, 1204, the penetrating member 1216 is used to pass from the source lumen 1206 to the target lumen 1208 in the alignment direction in FIG. 18d. In FIG. 18e, a guidewire 1220 is advanced through the penetrating member 1216, which is a needle, and into the target lumen 1208. The guide wire 1220 advances through the penetrating member 1216 and into the volume defined between the members of the SCM 1210. In FIG. 18f, the SCM 1210 is retracted from its expanded configuration, snaring the guide wire 1220 and securing it. In FIG. 18g, the target catheter 1204 is removed and the guide wire 1220 is advanced through the target lumen 1208. The source catheter 1202 is also removed.

Electrode Fabrication

In a further aspect of the present invention, a method the creation of electrodes on a small diameter catheter with sufficient accuracy to guide the creation of a conduit between two vessels or cavities (an anastomosis) is described.

In an embodiment, this aspect of the invention provides for apparatus in the form of medical devices each comprising an elongated shaft assembly, typically in the form of a catheter that comprises functional elements at the distal portion and a user or operator interface at the proximal terminus. The user interface may comprise a handle, handle assembly or hub.

Figure 19:
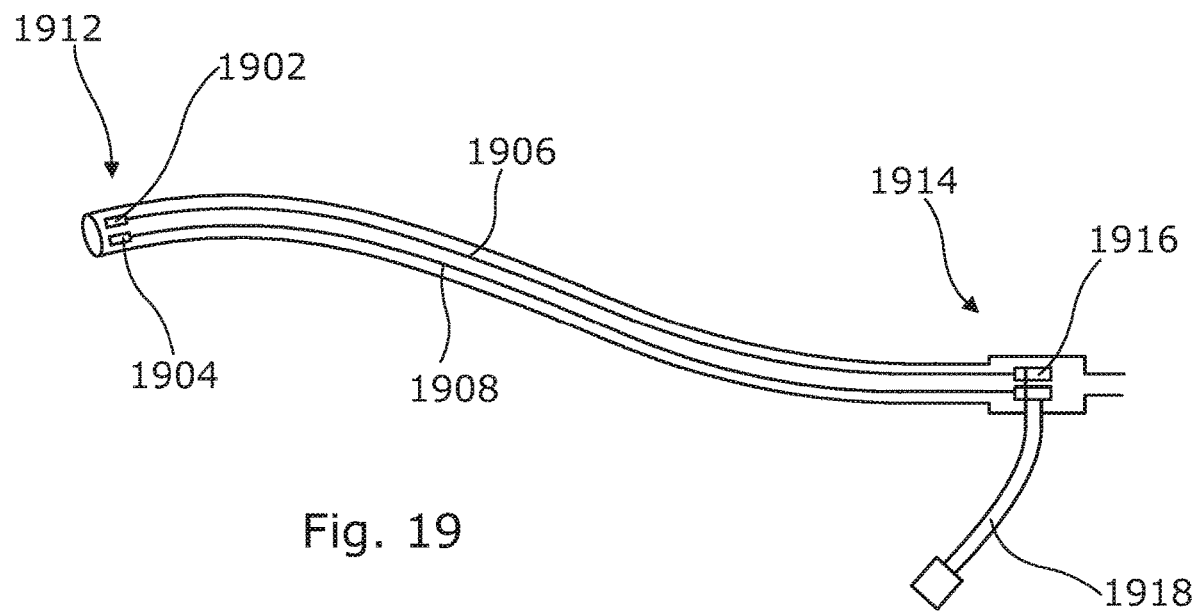
FIG. 19 is a representation of a catheter having printed electrodes according to an embodiment of the invention.

One embodiment of the present invention is shown in FIG. 19.

Figure 20:
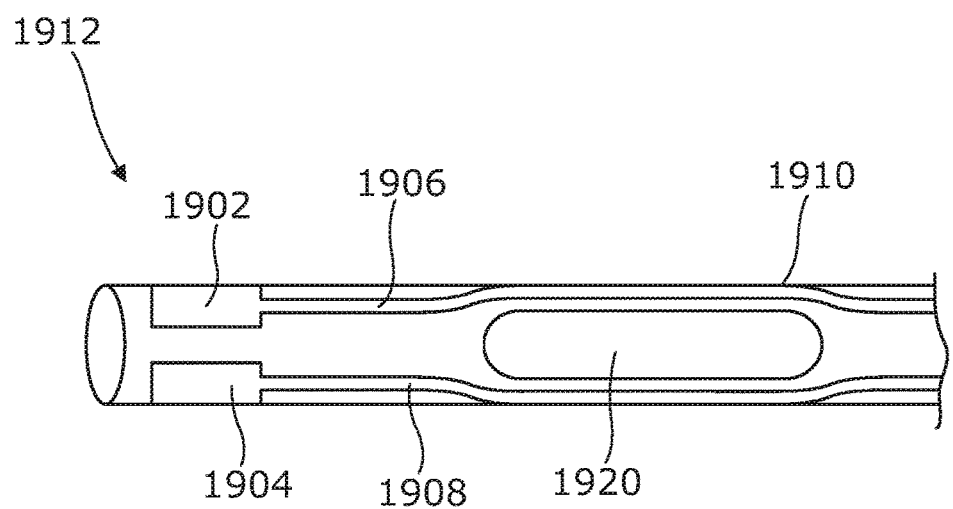
FIG. 20 is an expanded representation of the distal portion of the catheter having printed electrodes of FIG. 19.

The electrodes 1902, 1904 generate a spatially variant (or directional or asymmetric) electric field. While any suitable number of electrodes is envisaged, in the configuration shown the four electrodes are equally spaced around the circumference at the distal end of the catheter and these are connected to the electric generator via tracks 1906, 1908 on the catheter 1910 from the distal end 1912 to the proximal end 1914. These tracks 1906, 1908 may need to avoid the aperture 1920 where the crossing needle exits from the catheter. At the proximal end 1914, the tracks 1906, 1908 form connection pads 1916 where a multi-core conductor cable 1918 can be connected. FIG. 20 shows an expanded image of the distal portion 1912 of the catheter 1910.

In order to provide accurate alignment it is imperative that the electrodes are placed accurately, typically to better than 20 micron resolution, suitably to better than 10 micron resolution, suitably to better than 5 micron resolution, suitably to better than 2 micron resolution, and rotationally aligned to within 5 degrees, suitably to within 5 degrees, 4 degrees, 3 degrees, 2 degrees or 1 degree relative to their nominal positions on the cardinal points (i.e. diametrically opposed pairs, each pair at 90 degrees to the other).

Figure 21:
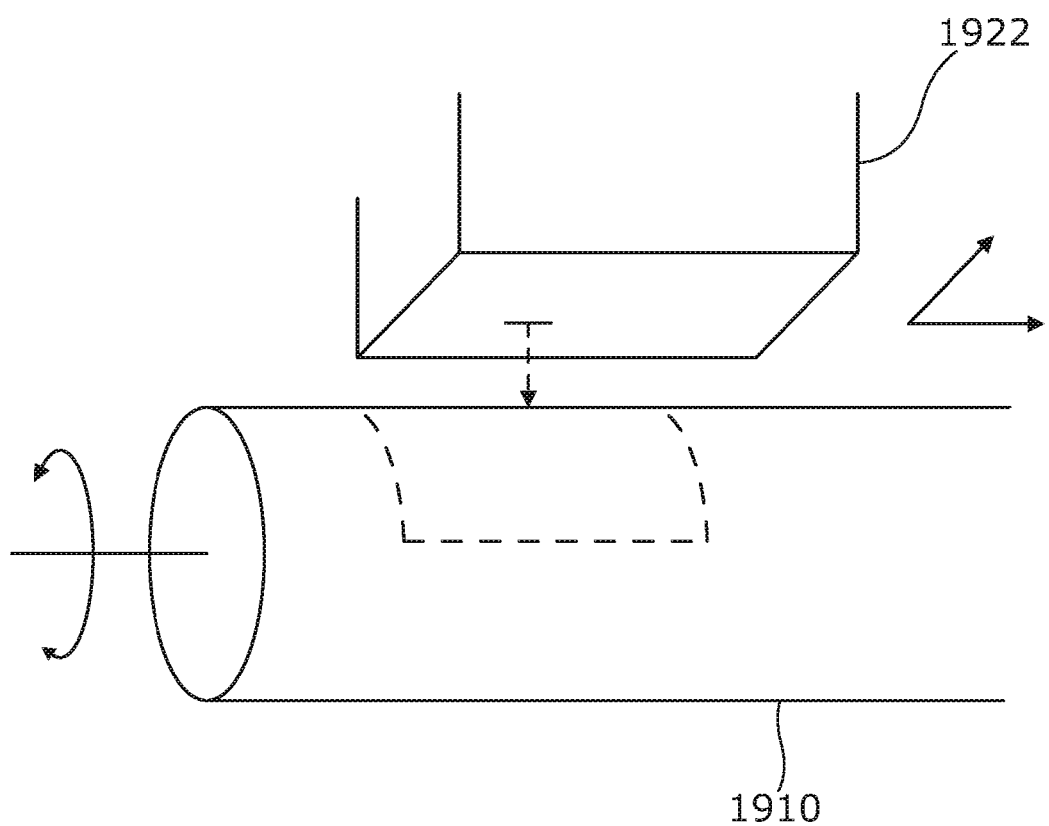
FIG. 21 is a representation of a method of fabricating the electrodes on the catheter of FIG. 19 using an ink-jet process.

In order to do achieve accurate placement of the electrodes they can be added to the catheter by a printing process. In one embodiment, conductive inks can be deposited by an ink-jet process, using a programmable printer that moves the ink-jet dispenser 1922 in a plane, whilst rotating the catheter 1910 (FIG. 21).

The catheter tubing will be made of any suitable material, suitably the catheter tubing is made of polyimide, nylon or other polymers. The ink can be based on any suitable material, suitably the ink is based on silver particles, gold particles or other conductive materials. The ink can also comprise a polymer medium which when cured remains flexible.

In another embodiment the printing method can comprise a continuous fluid extrusion. The printing method can be similar to that described in application US20100209318A1. In a preferred embodiment the elements and tracks are made with a silver based ink, as a base, with a gold based ink printed on top. Additionally an insulating material, such as polyurethane, can be printed selectively on top of the conductive tracks to expose only certain elements.

In another embodiment a primer is printed on the catheter tube, and subsequent immersion in an electro-less plating solution can deposit an electrode pattern.

In another embodiment a primer is printed on the catheter tube then activated with a laser, and subsequent immersion in an electro-less plating solution can deposit an electrode pattern.

In another embodiment, a mask containing a negative of the electrode pattern can be used, through which a metal such as gold, or silver, can be applied to the polymer substrate using sputter deposition (a form of physical vapour deposition (PVD)).

In another embodiment, a metal such as gold or silver, can be applied to the polymer substrate using sputter deposition after which a laser beam can be used to selectively ablate the metalized coating creating the electrode pattern.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

It will be appreciated that various changes and modifications can be made to the present invention without departing from the scope of the present application. The aspects and embodiments of the invention described above may be combined to form new aspects and embodiments. For example, embodiments of the invention may comprise any combination of features of the surgical device, processing system, self-centring mechanism, and/or the printed electrodes unless any of these features are explicitly indicated as being incompatible with one another.

The invention claimed is:

1. An apparatus for determining angular alignment between a source device and a target device, the apparatus comprising:
   the source device, the target device, and a processing system, the source device comprising:
   a first spatially variant field generator for generating a first spatially variant electric field; and
   a second spatially variant field generator for generating a second spatially variant electric field, wherein the second spatially variant electric field is angularly offset with respect to the first spatially variant electric field; and
   the target device comprising:
   at least one sensor configured to detect a first signal from the first spatially variant electric field and a second signal from the second spatially variant electric field,
   wherein the processing system determines an angular alignment between the source device and the target device based on the first and second signals from the first and second spatially variant electric fields detected by the target device, and
   wherein the first spatially variant field generator and the second spatially variant field generator have the same angular dependence.

2. The apparatus of claim 1, wherein each of the first spatially variant electric field and the second spatially variant electric field has a known angular dependence.

3. The apparatus of claim 1, wherein the first spatially variant electric field is angularly offset from the second spatially variant electric field by a preset angle.

4. The apparatus of claim 3, wherein the preset angle is 90°.

5. The apparatus of claim 1, wherein the first spatially variant field generator and the second spatially variant field generator are each at least one electrode.

6. The apparatus of claim 5, wherein the at least one electrode of the first spatially variant field generator is arranged to produce the first spatially variant electric field with angular and/or spatial dependence; and wherein the at least one electrode of the second spatially variant field generator is arranged to produce the second spatially variant electric field with angular and/or spatial dependence.

7. The apparatus of claim 6, wherein the first spatially variant electric field and the second spatially variant electric field with angular and/or spatial dependence are fields independently selected from dipole; quadrupole; or octopole.

8. The apparatus of claim 5, wherein the at least one electrode of the first spatially variant field generator and the at least one electrode of the second spatially variant field generator are each separately arranged to produce a dipole field.

9. The apparatus of claim 6, wherein the processing system is capable of operating the source device in at least a first mode and a second mode, wherein in the first mode, the first spatially variant field generator generates the first spatially variant electric and wherein in the second mode, the second spatially variant field generator generates the second spatially variant electric field.

10. The apparatus of claim 9, wherein the processing system further comprises a first switching system connected to the first spatially variant field generator and the second spatially variant field generator on the source device, the first switching system configured to switch the source device between the first mode and the second mode.

11. The apparatus of claim 10, wherein the first switching system operates the source device sequentially in the first mode and the second mode.

12. The apparatus of claim 11, wherein the source device is operated in the first mode until coarse angular alignment is achieved, and then the source device is operated in the second mode to achieve fine angular alignment, wherein a coarse angular alignment has a lower degree of accuracy in an angle of the angular alignment of the source device in comparison to a fine angular alignment.

13. The apparatus of claim 10, wherein the first switching system toggles between the first mode and the second mode so that a signal can be detected from both the first spatially variant electric field and the second spatially variant electric field simultaneously.

14. The apparatus of claim 10, wherein the first switching system operates the source device concurrently in the first mode and the second mode.

15. The apparatus of claim 14, wherein the first spatially variant electric field and the second spatially variant electric field are distinguishable by the sensor on the target device.

16. The apparatus of claim 15, wherein the first spatially variant electric field and the second spatially variant electric field are distinguishable by the sensor on the target device due to the first spatially variant electric field and the second spatially variant electric field having a different carrier frequency.

17. The apparatus of claim 9, wherein the sensor on the target device is connected to the processing system via a second switching system,
wherein the second switching system diverts a detected spatially variant signal detected at the sensor to one of two memory locations, and
wherein the second switching system diverts a detected signal to a first memory location of the two memory locations when the first switching system is operating in the first mode, and the second switching system diverts the detected signal to a second memory location of the two memory locations when the first switching system is operating in the second mode.

18. The apparatus of claim 17, wherein the second switching system is of a type selected from the group consisting of: hardware and software.

19. A method for determining an angle of alignment between a source device and a target device, the source device comprising a first spatially variant field generator for generating a first spatially variant electric field, and a second spatially variant field generator for generating a second spatially variant electric field, wherein the second spatially variant electric field is angularly offset with respect to the first spatially variant electric field, the target device comprising at least one sensor configured to detect a first signal from the first spatially variant electric field and a second signal from the second spatially variant electric field, the method comprising:
a) generating the first spatially variant electric field from the first spatially variant field generator on the source device;
b) detecting the first signal of the first spatially variant electric field using the sensor on the target device to provide a first spatially variant signal;
c) generating the second spatially variant electric field from the second spatially variant field generator on the source device;
d) detecting the second signal of the second spatially variant electric field using the sensor on the target device to provide a second spatially variant signal; and
e) determining the angle of alignment between the source device and the target device as a function of the detected first and second signals for the first spatially variant electric field and the second spatially variant electric field,
wherein the first spatially variant field generator and the second spatially variant field generator have the same angular dependence.

20. The method of claim 19, wherein when steps (a) to (d) are performed concurrently.

21. The method of claim 19, wherein when steps (a) to (e) are performed sequentially, after step (b) the first spatially variant electric field is switched off prior to the second signal being generated by the second spatially variant electric field.

22. The method of claim 19, wherein, steps (a) to (d) are repeated.

23. The method of claim 19, wherein when the first spatially variant electric field is angularly offset from the second spatially variant electric field by approximately 90° and wherein the angle of alignment is calculated as a function of the detected first and second signals in steps (b) and (d) using the formula:

$$\text{angle of alignment} = \arctan(\text{the first spatially variant signal}, \text{the second spatially variant signal}).$$

24. The method of claim 23, wherein an angular dependence of the first spatially variant electric field and the second spatially variant electric field is the same.

25. The method of claim 24, wherein the angular dependence of the first spatially variant electric field and the second spatially variant electric field is sinusoidal.

26. The method of claim 23, wherein a desired angle of alignment is offset from that indicated by the first spatially variant electric field and the second spatially variant electric field by an angle defined by an offset angle, the angle of alignment is calculated as a function of the detected first and second signals in steps (b) and (d) using the formula:
the angle of alignment=the offset angle+arctan (the first spatially variant signal,
the second spatially variant signal).

27. The method of claim 19, wherein the angle of alignment is displayed on a display.

28. A processing system for use in an apparatus for determining angular alignment between a source device and a target device,
wherein the source device comprises a first spatially variant field generator for generating a first spatially variant electric field and a second spatially variant field generator for generating a second spatially variant electric field, the second spatially variant electric field being angularly offset with respect to the first spatially variant electric field,
wherein the target device comprises at least one sensor configured to detect a first signal from the first spatially variant electric field and a second signal from the second spatially variant electric field,
wherein the processing system determines an angular alignment between the source device and the target device based on the first and second signals from the first and second spatially variant electric fields detected by the target device, and wherein the first spatially variant field generator and the second spatially variant field generator have the same angular dependence.

29. The apparatus of claim 1, further comprising a display.

30. An apparatus for determining angular alignment between a source device and a target device, the apparatus comprising:
the source device, the target device, and a processing system,
wherein the source device comprises a first spatially variant field generator for generating a first spatially variant electric field and a second spatially variant field generator for generating a second spatially variant electric field, the second spatially variant electric field being angularly offset with respect to the first spatially variant electric field,
wherein the target device comprises at least one sensor configured to detect a first spatially variant signal from the first spatially variant electric field and a second spatially variant signal from the second spatially variant electric field,
wherein the processing system determines an angular alignment between the source device and the target device based on the first and second spatially variant signals from the first and second spatially variant electric fields detected by the target device,
wherein an alignment is determined by the processing system,
wherein the alignment is calculated as a function of the detected first and second spatially variant signals, and
wherein the function is an inverse trigonometric function.

31. The apparatus of claim 30, wherein the inverse trigonometric function is arctan.

32. The apparatus of claim 30, wherein the alignment is calculated using the formula:

the alignment angle=an offset angle+arctan(the first spatially variant signal, the second spatially variant signal).

33. A method for determining an angle of alignment between a source device and a target device, the source device comprising a first spatially variant field generator for generating a first spatially variant electric field, and a second spatially variant field generator for generating a second spatially variant electric field, wherein the second spatially variant electric field is angularly offset with respect to the first spatially variant electric field, the target device comprising at least one sensor configured to detect a first spatially variant signal from the first spatially variant electric field and a second spatially variant signal from the second spatially variant electric field, the method comprising:

a) generating the first spatially variant electric field from the first spatially variant field generator on the source device;
b) detecting the first spatially variant signal of the first spatially variant electric field using the sensor on the target device to provide the first spatially variant signal;
c) generating the second spatially variant electric field from the second spatially variant field generator on the source device;
d) detecting the second spatially variant signal of the second spatially variant electric field using the sensor on the target device to provide the second spatially variant signal; and
e) determining the angle of alignment between the source device and the target device as a function of the detected first and second spatially variant signals for the first spatially variant electric field and the second spatially variant electric field,
wherein a desired alignment is offset from that indicated by the first spatially variant electric field and the second spatially variant electric field by an angle defined by an offset angle, the angle of alignment is calculated as a function of the detected first and second spatially variant signals in steps (b) and (d), and
wherein the function is an inverse trigonometric function.

34. The method of claim 33, wherein the inverse trigonometric function is arctan.

35. The method of claim 33, wherein the angle of alignment is calculated using the formula:

the angle of alignment=the offset angle+arctan(the first spatially variant signal, the second spatially variant signal).

* * * * *